(12) United States Patent
Yager et al.

(10) Patent No.: US 6,695,147 B1
(45) Date of Patent: *Feb. 24, 2004

(54) ABSORPTION-ENHANCED DIFFERENTIAL EXTRACTION DEVICE

(75) Inventors: Paul Yager, Seattle, WA (US); James P. Brody, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/416,072

(22) Filed: Oct. 12, 1999

Related U.S. Application Data

(63) Continuation of application No. 08/876,038, filed on Jun. 13, 1997, now Pat. No. 5,971,158.
(60) Provisional application No. 60/019,904, filed on Jun. 14, 1996.

(51) Int. Cl.[7] .................................................. B03B 5/00
(52) U.S. Cl. ..................... 209/455; 209/208; 209/210; 210/198.1; 210/645; 435/29
(58) Field of Search ................................. 209/155, 156, 209/157, 159, 160, 161, 208, 210; 210/198.1, 500.26, 634, 644, 645; 435/29

(56) References Cited

U.S. PATENT DOCUMENTS

| 3,449,938 A | 6/1969 | Giddings ........................ 73/23 |
| 4,147,621 A | 4/1979 | Giddings ................... 210/22 C |
| 4,214,981 A | 7/1980 | Giddings .................... 209/155 |

(List continued on next page.)

FOREIGN PATENT DOCUMENTS

| EP | 0 381 501 | 8/1990 | |
| EP | 0 645 169 | 3/1995 | |
| SU | 1623758 | 1/1991 | ................. 209/155 |

(List continued on next page.)

OTHER PUBLICATIONS

Afromowitz, M.A. and Samaras, J.E. (1989), "Pinch Field Flow Fractionation Using Flow Injection Techniques," *Separation Science and Technology* 24(5 and 6):325–339.
Brody, J.P. and Yager, P. (1996) *Solid State Sensor and Actuator Workshop*, Hilton Head Island, SC, Jun. 3–6, 1996, pp. 105–108.
Elwenspoek, M. et al. (1994), "Towards integrated microliquid handling systems," *J. Micromech. Microeng.* 4:227–245.
Faucheux, L.P. et al. (1995), "Optical Thermal Ratchet," *Phys. Rev. Lett.* 74(9):1504–1507.

(List continued on next page.)

*Primary Examiner*—Donald P. Walsh
*Assistant Examiner*—Kaitlin Joerger
(74) *Attorney, Agent, or Firm*—Seed IP Law Group PLLC

(57) ABSTRACT

This invention provides an extraction device and a method for extracting desired particles from a sample stream containing the desired particles. The device has a sample stream inlet, an extraction stream inlet, and an extraction channel in fluid communication with the sample stream inlet and the extraction stream inlet. The extraction channel is for receiving a sample stream from the sample stream inlet in adjacent laminar flow with an extraction stream from the extraction stream inlet. A sequestering material within the extraction channel captures desired particles in the extraction stream. A by-product stream outlet in fluid communication with the extraction channel receives a by-product stream comprising at least a portion of the sample stream form which desired particles have been extracted. A product outlet in fluid communication with the extraction channel receives a product which has the sequestering material and at least a portion of the desired particles.

26 Claims, 12 Drawing Sheets

U.S. PATENT DOCUMENTS

| | | | |
|---|---|---|---|
| 4,250,026 A | 2/1981 | Giddings et al. | 209/155 |
| 4,726,929 A | 2/1988 | Gropper et al. | 422/68 |
| 4,737,268 A | 4/1988 | Giddings | 209/12 |
| 4,830,756 A | 5/1989 | Giddings | 210/739 |
| 4,894,146 A | 1/1990 | Giddings | 209/12 |
| 4,894,172 A | 1/1990 | Williams | 209/155 X |
| 5,039,426 A | 8/1991 | Giddings | 210/695 |
| 5,141,651 A | 8/1992 | Giddings | 210/748 |
| 5,156,039 A | 10/1992 | Giddings | 73/1 R |
| 5,193,688 A | 3/1993 | Giddings | 209/210 X |
| 5,240,618 A | 8/1993 | Caldwell et al. | 210/748 |
| 5,250,263 A | 10/1993 | Manz | 422/81 |
| 5,288,463 A | 2/1994 | Chemelli | 422/58 |
| 5,304,487 A | 4/1994 | Wilding et al. | 435/291 |
| 5,465,849 A | 11/1995 | Wada et al. | 209/214 |
| 5,480,614 A | 1/1996 | Kamahori | 422/70 |
| 5,498,392 A | 3/1996 | Wilding et al. | 422/68.1 |
| 5,585,069 A | 12/1996 | Zanzucchi et al. | 422/100 |
| 5,599,432 A | 2/1997 | Manz et al. | 204/451 |
| 5,635,358 A | 6/1997 | Wilding et al. | 435/7.2 |
| 5,837,200 A | * 11/1998 | Diessel et al. | 209/155 X |
| 5,914,262 A | * 6/1999 | MacMichael et al. | 209/3.1 X |

FOREIGN PATENT DOCUMENTS

| | | |
|---|---|---|
| WO | 93/22053 | 11/1993 |
| WO | 93/22054 | 11/1993 |
| WO | 93/22055 | 11/1993 |
| WO | 93/22058 | 11/1993 |
| WO | 93/22421 | 11/1993 |
| WO | 96/04547 | 2/1996 |
| WO | 96/12540 | 5/1996 |
| WO | 96/12541 | 5/1996 |
| WO | 96/15576 | 5/1996 |

OTHER PUBLICATIONS

Forster, F.K. et al. et al. (1995), "Design, Fabrication and Testing of Fixed Valve Micro–Pumps," Proc. of the ASME Fluids Eng. Div. FED–vol. 234:39–44.

Fuh, C.B. et al. (1993), "Rapid Diffusion Coefficient Measurements Using Analytical SPLITT Fractionation: Application to Proteins," Analy. Biochem. 208:80–87.

Giddings, J.C. (1993), "Field–Flow Fractionation: Analysis of Macromolecular, Colloidal and Particulate Materials," *Science* 260:1456–1465.

Giddings, J.C. (1985), "Optimized Field–Flow Fractionation System Based on Dual Stream Splitters," *Anal. Chem.* 57:945–947.

Giddings, J.C. et al. (1983), "Outlet Stream Splitting for Sample Concentration in Field–Flow Fractionation," *Separation Science and Technology* 18:293–306.

Giddings, J.C. (1988), "Continuous Separation in SplitFlow Thin (SPLITT) Cells: Potential Applications to Biological Materials," Sep. Sci Technol. 23(8&9):931–943.

Gravesen, P. et al. (1993), "Microfluidics—a review," J. Micromech. Microeng. 3:168–182.

Harrison, D.J. et al. (1993), "Micromachining a Miniaturized Capillary Electrophoresis–Based Chemical Analysis System on a Chip," Science 261:895–897.

Kittilsland, G. (1990), "A Sub–micron Particle Filter in Silicon," Sensors and Actuators A21–A23:904–907.

Leff, H.S. and Rex, A.F. (1990), "Resource Letter MD–1: Maxwell's demon," Am. J. Phys. 58(3):201–209.

Levin, S. and Tawil, G. (1993), "Analytical SPLITT Fractionation in the Diffusion Mode Operating as a Dialysis–like System Devoid of Membrane. Application to Drug–Carrying Liposomes," *Anal. Chem.* 65:2254–2261.

Manz, A. et al. (1994), "Electroosmotic pumping and electrophoretic separations for miniaturized chemical analysis systems," J. Micromech. Microeng. 4:257–265.

Manz, A. et al. (1993), "Planar Chips Technology for Miniaturization of Separation Systems: A Developing Perspective in Chemical Monitoring," Adv. Chromatogr. 33:1–66.

Ramsey, J.M. et al. (1995), "Microfabricated chemical measurement systems," Nature Med. 1(10):1093–1096.

Rousselet, J. et al. (1994), "Directional motion of brownian particles induced by a periodic asymmetric potential," Nature 370:446–448.

Shoji, S. and Esashi, M. (1994), "Microflow devices and systems," J. Micromech. Microeng. 4:152–171.

Springston, S.R. et al. (1987), "Continuous Particle Fractionation Based on Gravitational Sedimentation in SplitFlow Thin Cells," Anal. Chem. 59:344–350.

Verpoorte, E.M.J. et al. (1994), "Three–dimensional micro flow manifolds for miniaturized chemical analysis systems," J. Micromech. Microeng. 4:246–256.

Wallis, G. and Pomerantz, D.I. (1969), "Field Assisted Glass–Metal Sealing," J. Appl. Phys. 40(10):3946–3949.

Weigl, B.H. and Yager, P. (1996), "Silicon–Microfabricated Diffusion–Based Optical Chemical Sensor," presented at the Europtrode Conf., Zurich, Switzerland, Apr. 2–3, 1996.

Wilding, P. et al. (1994), "Manipulation and Flow of Biological Fluids in Straight Channels Micromachined in Silicon," Clin. Chem. 40(1):43–47.

Williams, P.S. et al. (1992), "Continuous SPLITT Fractionation Based on a Diffusion Mechanism," *Ind. Eng. Chem. Res.* 31:2172–2181.

Yue, V. et al. (1994), "Miniature Field–Flow Fractionation Systems for Analysis of Blood Cells," *Clin. Chem*40:1810–1814.

* cited by examiner

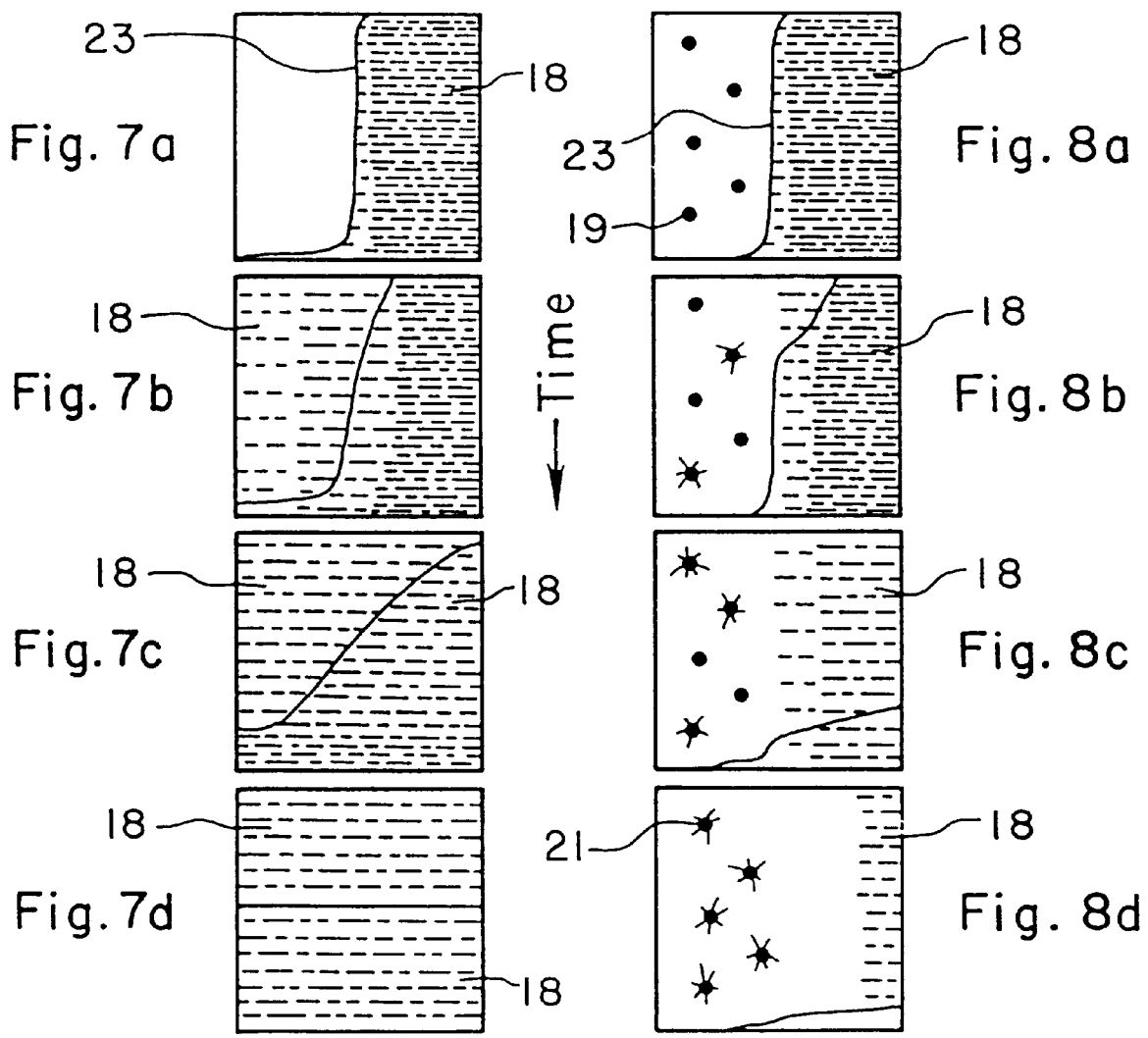

ABSORPTION-ENHANCED DIFFERENTIAL EXTRACTION DEVICE

CROSS-REFERENCE TO RELATED APPLICATIONS

This is a continuation of application U.S. Ser. No. 08/876,038 filed Jun. 13, 1997 now U.S. Pat. No. 5,971,158, which takes priority from U.S. provisional patent application No. 60/019,904 filed Jun. 14, 1996, which is incorporated herein in its entirety by reference.

This invention was made with government support under Army research contract DAMD17-94-J-4460 awarded by the U.S. Army. The government has certain rights in the invention.

FIELD OF THE INVENTION

This invention relates generally to extraction systems and methods for separating analytes from streams containing other constituents by differential transport principles such as diffusion and applied fields, providing an improved method involving the use of absorbents or adsorbents in the extraction stream. The devices and methods of this invention can be used for diagnostic and therapeutic/treatment purposes.

BACKGROUND OF THE INVENTION

Field flow fractionation devices involve particle size separation using a single inlet stream. See, e.g., Giddings, J. C., U.S. Pat. No. 3,449,938, Jun. 17, 1969, "Method for Separating and Detecting Fluid Materials"; Giddings, J. C., U.S. Pat. No. 4,147,621, Apr. 3, 1979, "Method and Apparatus for Field-Flow Fractionation"; Giddings, J. C., U.S. Pat. No. 4,214,981, Jul. 29, 1980, "Steric Field-Flow Fractionation"; Giddings, J. C. et al., U.S. Pat. No. 4,250,026, Feb. 10, 1981, "Continuous Steric FFF Device for The Size Separation of Particles"; Giddings, J. C. et al. (1983), "Outlet Stream Splitting for Sample Concentration in Field-Flow Fractionation," Separation Science and Technology 18:293–306; Giddings, J. C. (1985), "Optimized Field-Flow Fractionation System Based on Dual Stream Splitters," Anal. Chem. 57:945–947; Giddings, J. C., U.S. Pat. No. 4,830,756, May 16, 1989, "High Speed Separation of Ultra-High Molecular Weight Polymers by Hyperlayer Field-Flow Fractionation"; Giddings, J. C., U.S. Pat. No. 4,141,651, Aug. 25, 1992, "Pinched Channel Inlet System for Reduced Relaxation Effects and Stopless Flow Injection in Field-Flow Fractionation"; Giddings, J. C., U.S. Pat. No. 5,156,039, Oct. 20, 1992, "Procedure for Determining the Size and Size Distribution of Particles Using Sedimentation Field-Flow Fractionation"; Giddings, J. C., U.S. Pat. No. 5,193,688, Mar. 16, 1993, "Method and Apparatus for Hydrodynamic Relaxation and Sample Concentration in Field-Flow Fraction Using Permeable Wall Elements"; Caldwell, K. D. et al., U.S. Pat. No. 5,240,618, Aug. 31, 1993, "Electrical Field-Flow Fractionation Using Redox Couple Added to Carrier Fluid"; Giddings, J. C. (1993), "Field-Flow Fractionation: Analysis of Macromolecular, Colloidal and Particulate Materials," Science 260:1456–1465; Wada, Y. et al., U.S. Pat. No. 5,465,849, Nov. 14, 1995, "Column and Method for Separating Particles in Accordance with Their Magnetic Susceptibility"; Yve, V. et al. (1994), "Miniature Field-Flow Fractionation Systems for Analysis of Blood Cells," Clin. Chem. 40:1810–1814; Afromowitz, M. A. and Samaras, J. E. (1989), "Pinch Field Flow Fractionation Using Flow Injection Techniques," Separation Science and Technology 24(5 and 6):325–339.

Thin-channel split flow fractionation (SPLITT) technology also provides particle separation in a separation cell having a thin channel. A field force is exerted in a direction perpendicular to the flow direction. Particles travel from a particle-containing stream across a transport stream to a particle-free stream. The device for operating the process is generally fabricated from glass plates with teflon sheets used as spacers to form the channels. The channel depth can therefore be no smaller than the spacers, which are generally about 100 to 120 $\mu$m thick. See, e.g., Giddings, J. C., U.S. Pat. No. 4,737,268, Apr. 12, 1988, "Thin Channel Split Flow Continuous Equilibrium Process and Apparatus for Particle Fractionation"; Giddings, J. C., U.S. Pat. No. 4,894,146, Jan. 16, 1990, "Thin Channel Split Flow Process and Apparatus for Particle Fractionation"; Giddings, J. C., U.S. Pat. No. 5,093,426, Aug. 13, 1991, "Process for Continuous Particle and Polymer Separation in Split-Flow Thin Cells Using Flow-Dependent Lift Forces"; Williams, P. S. et al. (1992), "Continuous SPLITT Fractionation Based on a Diffusion Mechanism," Ind. Eng. Chem. Res. 31:2172–2181; and Levin, S. and Tawil, G. (1993), "Analytical SPLITT Fractionation in the Diffusion Mode Operating as a Dialysis-like System Devoid of Membrane. Application to Drug-Carrying Liposomes," Anal. Chem. 65:2254–2261.

The object of this invention is to provide an improved extraction system utilizing differential transport principles in which the analyte can be extracted, detected and quantified. A further object of this invention is to provide an improved extraction system for purification and treatment of fluids, including bodily fluids such as blood.

All publications, patents and patent applications referred to herein are incorporated in their entirety by reference.

SUMMARY OF THE INVENTION

Differential extraction devices as described above allow desired particles to move from a sample stream into an extraction stream running in parallel laminar flow with the extraction stream. A simple embodiment of such systems uses a concentration gradient across the streams so that desired particles diffuse from the sample stream into the extraction stream. Other gradients and forces can also be used, e.g., magnetic, electrical, gravitational, dielectrical, sedimentation, shear, centrifugal force, temperature, pressure, and cross-flow gradients.

An improvement in the above processes provided herein is the addition of a sequestering material to the extraction stream.

The invention provides an extraction device for extracting desired particles from a sample stream containing said desired particles, said device comprising:

a. a sample stream inlet;
b. an extraction stream inlet;
c. an extraction channel in fluid communication with said sample stream inlet and said extraction stream inlet for receiving a sample stream from said sample stream inlet in adjacent laminar flow with an extraction stream from said extraction stream inlet;
d. a sequestering material within said extraction channel for capturing desired particles in said extraction stream;
e. a by-product stream outlet in fluid communication with said extraction channel for receiving a by-product stream comprising at least a portion of said sample stream from which desired particles have been extracted;
f. a product outlet in fluid communication with said extraction channel for receiving a product comprising said sequestering material and at least a portion of said desired particles.

A sequestering material is a material which captures, e.g., by adsorbing, binding or sticking to the desired particles, or by absorbing them. Enzymes, antibodies, antigens and other ligands for desired particles are known to the art and are useful sequestering materials for this invention. Any ligand known to the art for a desired particle may be used as a sequestering material. Such ligands may be added to the extraction stream "as-is" or may be immobilized on substrates such as polymeric beads, high molecular weight polymers, or other materials known to the art. "High molecular weight polymers" refers to those polymers of sufficient molecular weight that they do not substantially diffuse into the sample stream during their transit through the device. Examples of high molecular weight polymers include but are not limited to high molecular weight dextrans, high molecular weight polypeptides, and high molecular weight nucleic acids. The sequestering material may also be an absorbent material such as activated charcoal, or porous polymers. Absorbents or adsorbents may be either specific to a particular particle type, such as an antibody, or nonspecific, such as activated charcoal.

The sequestering material is preferably substantially non-diffusing, i.e., should diffuse sufficiently slowly that it does not cross from the extraction stream into the sample stream to any significant degree, so that it does not become detectable in the by-product stream, or does not interfere with analysis of analytes in the by-product stream.

The sequestering material captures the desired particles by preventing them from exiting the device with the exiting by-product stream. The desired particles may be loosely bound to the sequestering material, so long as the sequestering material retains the particles long enough to prevent them from exiting with the by-product stream. The desired particles may be reversibly bound to or captured by the sequestering material so that they can be removed for further analysis or to allow re-use of the sequestering material.

Differential extraction devices fabricated on the microscale provide numerous advantages over the larger devices discussed above. Such microfabricated devices are described in application Ser. No. 08/663,916 filed Jun. 14, 1996, which is specifically incorporated herein in its entirety by reference along with all references incorporated therein by reference. Definitions of terms used in that application as applied to the microscale structures disclosed therein are applicable herein to macroscale structures as well as microscale structures. "Macroscale structures" are defined herein as structures larger than microscale structures but still small enough to permit laminar flow.

The desired particles in this invention may be analytes or they may be substances that interfere with analytes. They may also be particles desired to be recovered and used for another purpose, or toxins, such as poisons or metabolites in a patient's blood. For example, this invention can be used to detoxify blood, e.g., remove toxic metals from blood, or to detoxify other bodily fluids, e.g., to perform hemodialysis. This invention can be used in waste-water treatment, e.g., to remove impurities from water. Alternatively, this invention can be used to remove a drug or other product produced by microorganisms, e.g., bacterial cells, in a fermentation reactor without damaging the microorganisms. Such treatments can be performed in a continuous fashion.

This invention also provides a method for extraction of at least a portion of desired particles from a sample stream comprising said desired particles, comprising the steps of:
   a. introducing the sample stream into the sample stream inlet of an extraction device as described above;
   b. introducing an extraction stream into the extraction channel of said extraction device; and
   c. introducing into said extraction channel a sequestering material for capturing the desired particles such that the desired particles are captured by the sequestering material, and such that said extraction stream, comprising said sequestering material and at least a portion of said desired particle, exits said device as a product stream, and such that said sample stream from which desired particles have been extracted, exits said device as a by-product stream.

The device and method of the present invention provide a means for performing affinity chromatography. As is understood by those in the art, affinity chromatography refers to a method of purifying or isolating desired substances and generally involves covalently attaching a specific ligand to an insoluble inert support. In affinity chromatography the ligand must have a high affinity for the desired substance, so that on passage in solution down a column the desired substance is preferentially retained by the ligand.

The present invention provides a device and method for performing affinity chromatography, however with at least one particular advantage. The extraction of a desired substance (particles) can be performed in a continuous fashion. The sample streams and extraction streams of the present invention can be run continuously through the device. Art-known affinity chromatography involves multiple steps, e.g., loading the ligand onto the inert material, flushing the column, loading the sample, rinsing, then rinsing again to release the desired substance, with product loss occurring at each step usually. In the device of the present invention, for example, a virus can be extracted from whole blood by 1) introducing an extraction stream comprising an antibody to the virus immobilized on beads and a sample stream of whole blood into the device and 2) after transfer of the virus particles to the extraction stream, releasing them by changing the pH of the solution. The beads can be chosen, for example, so that they will fall to the bottom of the channel or they can be magnetic and therefore pulled to one side of the channel with a magnet.

The sequestering material can be present in the extraction stream prior to the extraction stream's being introduced into the extraction channel. Alternatively, the sequestering material can be added to the extraction stream by suspending or dissolving the sequestering material in a liquid which is introduced into the extraction stream, which is already in the extraction channel, via the extraction stream inlet.

The extraction system of this invention in simplest concept is illustrated by a diffusion extraction device comprising microchannels in the shape of an "H". A mixture of particles suspended in a sample stream enters the extraction channel (the crossbar of the "H") from one of the arms, e.g., the top left, and an extraction stream (a dilution stream) enters from the bottom left. The two streams flow together in the extraction channel; however, due to the small size of the channels, the flow is laminar and the streams do not mix. The sample stream exits as by-product stream at the upper right and the extraction stream exits as product stream from the lower right. While the streams are in adjacent laminar flow in the extraction channel, particles having a greater diffusion coefficient (smaller particles such as albumin, sugars and small ions) have time to diffuse into the extraction stream, while the larger particles (e.g., blood cells) remain in the sample stream. Particles in the exiting extraction stream (now called the product stream) may be analyzed without interference from the larger particles.

In this patent application, the flow direction of a channel is called its length (L). The channel dimension in the direction of particle transport at right angles to the length (L) is called its depth (d). The third channel dimension at right angles to both the length and depth is called its width (w). The depth (d) is therefore perpendicular to the plane of interface of the sample and extraction streams. Table 1 lists other abbreviations used herein.

TABLE 1

| | |
|---|---|
| V | Volume |
| $V_{ss}$ | Sample stream flow rate (m³/s) |
| $V_{es}$ | Extraction stream flow rate (m³s) |
| $V_{ps}$ | Product stream flow rate (m³s) |
| $V_{bps}$ | By-product stream flow rate (m³s) |
| $V_{ind}$ | Indicator dye stream flow rate (m³s) |
| $V_{ds}$ | Detection stream flow rate (m³s) |
| $C_{i,ss}$ | Sample stream constituent i concentration (kg/kg) |
| $C_{i,es}$ | Extraction stream constituent i concentration (kg/kg) |
| $C_{i,bps}$ | By-product stream constituent i concentration (kg/kg) |
| $C_{i,ps}$ | Product stream constituent i concentration (kg/kg) |
| $C_{dye,ind}$ | Indicator stream dye concentration (kg/kg) |
| $C_{i,ds}$ | Detector stream constituent i concentration (kg/kg) |
| d | Diffusion direction extraction channel depth (m) |
| w | Extraction channel width (m) |
| L | Extraction channel length (m) |
| $a_\%$ | Percentage deviation from equilibrium concentration |
| $L_{a\%}$ | Device length required to achieve $a_\%$ (m) |
| $z_s$ | Interface streamline location between sample and extraction streams at the extraction channel entrance (m) |
| $z_p$ | Interface streamline location between the by-product and product streams (m) |
| P | Absolute pressure within the fluid stream (Pa) |
| $\Delta p$ | Differential pressure between the entrance and exit of the extraction channel (Pa) |
| $D_i$ | Binary diffusion coefficient of constituent i (m²/s) |
| $\mu$ | Fluid viscosity (Pa · s) |
| $\rho$ | Fluid density (kg/m³) |
| $\xi$ | Equilibrium normalized constituent concentration for an infinite length extraction channel (dimensionless) |
| $\tilde{c}$ | Normalized constituent concentration (dimensionless) |
| x | Channel length coordinate direction (flow direction) |
| y | Channel width coordinate direction |
| Z | Diffusion direction coordinate |
| $\tilde{x},\tilde{z}$ | Non-dimensional normalized variables (dimensionless) |
| w/d | Aspect ratio |
| D | Diffusion coefficient |
| Re | Reynolds number |
| T | Temperature |
| u | Axial velocity |
| $\overline{V}$ | Average velocity |

The length of the extraction channel and the extraction channel flow velocity are key parameters determining the amount of time the particles have to diffuse into the extraction stream. The sequestering material provides for increased diffusion of the desired particles by decreasing the effective concentration of the desired particles in the extraction stream. That is, the sequestering material effects a shift in the equilibrium (in a positive direction) of diffusion of the desired particles into the extraction stream.

The particles in the case described above are differentially transported from the sample stream to the extraction stream using diffusion as the transport mechanism. Other means for effecting differential transport of the desired particles can also be used. The term "differential transport" means that a portion of the desired particles are transported from the sample stream into the extraction stream to the substantial exclusion of the undesired particles. For example, magnetic, electrical or other forces can be applied across the extraction stream, temperature gradients can be used, or absorbent or adsorbent materials such as antibodies can be added to the extraction stream to capture the desired particles.

The sample stream and extraction stream inlets and the byproduct stream and product stream outlets may comprise channels, reservoirs, ports, or other containers. The sample stream inlet is designed to receive a sample stream containing "desired particles," e.g., particles it is desired to extract so that their presence may be detected. The sample stream also includes other particles which are not extracted, termed "undesired particles" herein. These undesired particles include particles which might interfere with the detection of the desired particles. In a preferred embodiment, the sample stream comprises whole blood. The desired particles may be albumin or other blood plasma components, and the undesired particles may be blood cells. The device is especially useful for obtaining cell-free plasma components from whole blood. Other fluids for which the present invention is useful include solutions or suspensions of DNA fragments of different lengths, proteins of varying sizes, or heterogeneous chemical reaction mixtures. Sample streams useful in the practice of this invention include fermentation broths, raw sewage, liquefied food samples, soil samples and biological fluids such as sputum, urine, and cerebral spinal fluid.

The term "particles" refers to molecules; cells; macromolecules such as proteins, nucleic acids and complex carbohydrates; small molecules comprised of one to several atoms; and ions. The particles may be suspended or dissolved in the stream. The term "stream" refers to a carrier fluid such as water or other liquid, air or other gas, containing desired and/or undesired particles. The term "particles" as used herein does not include the molecules of the carrier stream.

The term "extraction" refers to the transfer of at least a portion, i.e., a detectable portion, of desired particles from the sample stream to the extraction stream, to the substantial exclusion of undesired particles. It is recognized that undesired particles may be transported into the extraction stream, particularly those that diffuse faster than the desired particles; however, the presence of such undesired particles will be minimized such that they do not interfere with detection or subsequent processing of the streams containing the desired particles. The transfer of undesired particles from the sample stream to the extraction stream can be minimized by pre-loading the extraction stream with such undesired particles. Pre-loading the extraction stream with undesired particles may be preferable in embodiments wherein the by-product stream is of interest, e.g., for further use or analysis. For example, if blood is to be returned to a patient's body, the extraction stream preferably contains the appropriate concentrations of electrolytes, as will be understood by those of skill in the art. The sequestering material increases the efficiency of separation of the desired particles from the sample by decreasing the effective concentration of the desired particles in the extraction stream.

The term "extraction efficiency" refers to the percentage of desired particles in the sample which are transferred to the extraction stream and exit in the product stream. Extraction efficiency can be increased by using a sequestering material.

The term "laminar flow" of two streams means stable, side-by-side, non-recirculating, flow of two streams without mixing. There are no zones of re-circulation, and turbulence is negligible. As is known to the art, the Reynolds number of a flow is the ratio of inertial forces to viscous forces. For flow through a duct, the Reynolds number is calculated using the equation Re=$\rho d(\overline{V}/\mu)$ where Re is the Reynolds number, $\rho$ is the mass density of the fluid, d is a typical cross-sectional dimension of the duct depending on the shape of the duct, $\overline{V}$ is the mean velocity over the duct cross-section and $\mu$ is the viscosity.

As the Reynolds number is reduced, flow patterns depend more on viscous effects and less on inertial effects. Below a certain Reynolds number (based on lumen size for a system of channels with bends and lumen size changes), inertial effects are insufficient to cause phenomena indicative of their significant presence such as laminar recirculation zones and turbulent flow. Therefore, non-turbulent, laminar non-recirculating flow occurs in the extraction devices discussed herein. In such devices minimal dispersive mixing occurs as a result of the viscous flow velocity profiles present within any laminar viscous flow. This allows two laminar non-recirculating fluid streams to flow down an extraction channel for the purpose of desired particle extraction from one stream to the other.

The streams may be separated at the end of the conduit at any arbitrary location by precise regulation of the exit flow rate of the outlets, something which is not possible at higher Reynolds numbers not satisfying the non-recirculating and non-turbulent criteria.

The extraction stream inlet is designed to receive an extraction stream capable of accepting desired particles when in laminar flow contact with the sample stream. The extraction stream can be any fluid capable of accepting particles being transported from the sample stream. The extraction stream contains sequestering material which binds desired particles which have been transported from the sample stream to the extraction stream. Preferred extraction streams are water and isotonic solutions such as physiological saline. Other useful extraction streams comprise organic solvents such as acetone, isopropyl alcohol, supercritical carbon dioxide or ethanol. Air and other gases may also be used as sample and extraction stream carriers.

The by-product stream comprises at least a portion of said sample stream from which desired particles have been extracted, and may or may not, as discussed below, include a fraction of the extraction stream into which desired particles have been conveyed from the sample stream. The sequestering material effects greater extraction of the desired particles from the sample, thereby yielding a more pure by-product stream. If an excess of sequestering material is used and it has a high binding constant for the desired particles, then essentially all of the desired particles in the sample stream can be extracted from the sample stream upon treatment of the sample just once, depending on flow rate and extraction channel length. Without the sequestering material and assuming equal flow rates of sample and extraction fluids, the equilibrium concentration of the desired particles is 50% in the extraction stream. That is, at most, only 50% of the desired particles diffuse into the extraction stream. Therefore, without the sequestering material the sample has to be treated at least five times to remove 97% of the desired particles from the sample.

The by-product stream outlet is designed to conduct the by-product stream (composed of the sample stream and perhaps a portion of the extraction stream) that is removed from the extraction channel to disposal, recycle, or other system component, for further processing.

The product stream comprises at least a portion of said desired particles and the sequestering material. The product stream outlet, which as stated above, may comprise a product stream channel, is designed to conduct the product stream containing a detectable quantity of desired particles to a detection or further processing area or system component. A sufficient quantity of the extraction stream must be present in the product stream, comprising a sufficient quantity of desired particles, such that the presence of the desired particles is detectable in the product stream by means known to the art.

The product stream may be conducted to a reservoir chamber, or other device where it may be further treated, e.g., by separating the sequestering material from the desired particles, mixing, separating, analyzing, heating or otherwise processing, for example as disclosed in Wilding, P., et al. U.S. Pat. No. 5,304,487 issued Apr. 19, 1994, incorporated herein by reference. The by-product stream may also be conducted to a reservoir chamber or other container or apparatus for further treatment.

The devices of this invention may be "microfabricated," which refers to devices capable of being fabricated on silicon wafers readily available to those practicing the art of silicon microfabrication and having the feature sizes and geometries producible by such methods as LIGA, thermoplastic micropattern transfer, resin based microcasting, micromolding in capillaries (MIMIC), wet isotropic and anisotropic etching, laser assisted chemical etching (LACE), and reactive ion etching (RIE), or other techniques known within the art of microfabrication. In the case of silicon microfabrication, larger wafers will accommodate a plurality of the devices of this invention in a plurality of configurations. A few standard wafer sizes are 3", 4", 6", and 8". Application of the principles presented herein using new and emerging microfabrication methods is within the scope and intent of the claims hereof.

In a preferred embodiment, called the "H-filter device" herein, the inlet and outlet channels are between about 2 to 3 times the maximum-sized stream particulate diameter and about 100 micrometers in width and between about 2 to 3 times the diameter of the maximum-sized particles and less than about 100 micrometers in depth, and the extraction channel is between about 2 to 3 times the diameter of the maximum-sized particles and about 2/3 the wafer thickness in width, between about 2 to 3 times the diameter of the maximum-sized particles and less than about 100 micrometers in depth, and between about 4 and about 10 times the diameter of the maximum-sized particles and less than or equal to 5 mm long.

In a second embodiment in which the particle transport direction is rotated 90 degrees from that of the "H-filter device" design, called the "flat extraction device" or "flat filter device" herein, the inlet channels have a width equal to the extraction channel width at the entrance to the extraction channel of preferably between 2 and 3 particle diameters and about 500 micrometers, and the extraction channel is preferably between about 2 and 3 times the diameter of maximum-sized particles and less than or equal to 5 mm in width, between about 2 and 3 times the diameter of the maximum-sized particles and less than about 100 micrometers in depth, and at least about 4 times the diameter of the maximum-sized particles in length.

The extraction channel receives the inflow of the sample and extraction streams from the sample and extraction stream inlets and conducts these streams in adjacent laminar flow for a distance sufficient to allow extraction of the desired particles into the extraction stream. The length of the extraction channel can be increased by forming it in a convoluted geometry, e.g., serpentine (set of "hairpin" turns) or coiled, as are the flow channels disclosed in Weigl et al., U.S. patent application Ser. No. 08/829,679, filed Mar. 31, 1997 and PCT Application No. PCT/US97/05245, filed Mar. 31, 1997, which are incorporated herein by reference.

The width and depth of the extraction stream channel and product outlet channels must be large enough to allow passage of the desired particles, the sequestering material, and any complex of the desired particles with the sequestering material.

If the width dimension is in the wafer thickness direction, as it is in the H-filter device embodiment, then for the silicon microfabricated embodiments of the microscale extraction devices of the present invention, the widths of the sample, extraction, product, and by-product channels, inlets and outlets are less than the silicon wafer thickness, i.e., about 300 micrometers. Alternatively, if the device is made from other materials, preferably moldable materials such as plastic, or in the "flat extraction device" embodiment, then there is no theoretical maximum limit to the width. Widths up to 0.5 meter, 1 meter, and even greater are contemplated. The width has no theoretical maximum limit provided that one can control the delivery of fluids (sample stream and extraction stream) into the device, e.g., the flow rate of each fluid can be controlled across the width of the channel. The dimensions of the extraction channel are chosen to maintain laminar flow and uniform flow rate, e.g., no turbulence or build up of particles on channel walls.

If the depth dimension is in the wafer thickness direction, as it is in the "flat filter" embodiment, then for silicon microfabricated embodiments of the microscale extraction devices of the present invention, the depth of the sample, extraction, product, and by-product channels, inlets and exits is less than the silicon wafer thickness, i.e., about 300 micrometers. Preferably, for microfabricated devices, the depth, particularly of the extraction channel, is less than about 200 micrometers, and more preferably less than about 100 micrometers.

Some fields known to the art which may be used for differential transport of the particles in the devices of this invention are those produced by:

Sedimentation
Electrical potential
Temperature gradients
Cross Flow
Dielectrical gradients
Shear forces
Magnetic forces
Concentration gradients
Means for producing such fields are known to the art.

Because of the small size of the diffusion direction (depth) of the channels described herein, differential transport of desired particles by diffusion or other means occurs extremely rapidly, e.g., within less than about 300 seconds, and if desired, less than about one second. The presence of the sequestering material in the extraction stream provides for increased desired particle transport by lowering the effective concentration of the desired particles in the extraction stream, maximizing the effective concentration difference between the sample stream and the extraction stream. This maximizes the net transfer along the depth (diffusion dimension) of the extraction channel, thus providing rapid separation of desired particles from the sample.

The sample and extraction streams may have different properties, e.g., viscosities, densities, surface energies, homogeneities, chemical compositions and the like, which may affect the differential transport rates. System parameters may need to be adjusted and optimized to take account of these differing properties, as will be apparent to, and can be done without undue experimentation by, those skilled in the art.

The sample and extraction streams are kept in contact in the extraction channel for a period of time sufficient to allow at least an analyzable quantity, and preferably a major portion, of desired particles to be transported into the extraction stream. The flow rate of the product stream from the device may be between about 0.001 picoliter/sec and about 10 ml/sec or more in devices with large widths, e.g., greater than about 50 μm. For example, an optimal flow rate for the product stream can be about 200 nanoliters/sec. As is known in the art, even the very small amounts of analytes present in such small product streams may be detected by spectroscopic and other means.

The average flow velocity, $\overline{V}$, is chosen to fit the following relationship:

$$\overline{V} < f\frac{DL}{d^2}$$

where f is a time factor (proportionality constant) related to how long the two streams must be in contact with each other in order for a certain percentage of desired particles to be transferred from the sample stream to the extraction stream.

The volumetric flow rate (Q) per unit width (w) is thus limited to be less than f(DL)/d: Q=$\overline{V}$wd, Q/w=$\overline{V}$d $$\frac{Q}{w} < f\frac{DL}{d}$$

It may be convenient for calculation purposes to choose f=1, and calculate the maximum flow rate per unit width based thereon. For example, for biotin (with diffusion coefficient, D=500 μm²/sec in a channel of length (L)=1 cm and depth (diffusion dimension) (d)=10 μm, the maximum flow rate per unit width is approximately 500 picoliters/sec per μm of width.

From the above the following relationship can be derived:

$$d^2/D=2t$$

which means that a molecule will diffuse across distance d (the depth of the channel) in an average time of 2t.

A "major portion" of the desired particles is more than 50% of said particles present in the sample stream.

The sequestering material enhances the efficiency of the extraction process, allowing for greater than 50% extraction (the maximum extraction obtained with equal volumes of the sample and extraction stream, but without sequestering material or other differential transport forces, e.g., magnetic and electircal fields). Preferably, the sequestering material allows for extraction of greater than about 50% to about 80% of the desired particles. More preferably, the sequestering material allows for extraction of about 75% to about 95% of the desired particles. Most preferably, the sequestering material allows for extraction of about 85% to about 100% of the desired particles.

Successful operation of the invention described herein requires precise control of volume flow rates on three of the four channels of the device (i.e., sample, extraction, product, and by-product streams). The fourth channel need not and should not be regulated, as leaving this channel unregulated will allow the device to accommodate unpredictable changes in volume of the sample because of ΔV of mixing of the sample and extraction streams. Means for achieving precisely regulated flow rates are known to the art.

To aid in controlling the size of particles being transported to the product stream in a diffusion-based extraction system of this invention, and reduce the appearance of larger particles in the product stream, a fluid barrier may be created in the extraction channel. Such a fluid barrier is present when the extraction stream is present in sufficient volume to cause a portion of the extraction stream to flow through the by-product exit with the exiting by-product stream, as illustrated in FIG. 3. Smaller particles diffusing into the extraction stream must cross the width of this fluid barrier before being able to exit with the product stream. Such fluid barriers formed on a larger scale are discussed in Williams P. S., et al. (1992), "Continuous SPLITT Fractionation Based on a Diffusion Mechanism," Ind. Eng. Chem. Res. 2172–2181, incorporated herein by reference.

By controlling the flow rate of the sample and extraction streams, the ratio of volume from each that enters the extraction channel can be controlled. The volume ratio of the sample stream and the extraction stream can also be set by the geometry of the outlet and inlet channels for a fixed delivery pressure on the sample and extraction streams. The volume flow rate of the product and by-product streams may also be controlled by manipulating the product and by-product stream pressures or by using arbitrary port (inlet) pressures and altering the flow resistance of the inlets. Whatever the control mode, the inlet and outlet channels must satisfy the criteria for minimum channel dimensions based on the size of the particulate to be processed as described herein. If the volume of the extraction stream entering the extraction channel is greater than the volume of the sample stream, and the two exit streams are identical, a fluid barrier is formed. If the volume flow rate of the product stream is too small to accommodate the entire volume flow of the extraction stream then a fluid barrier will also be formed.

Extraction devices of this invention may comprise means for controlling the volume of extraction stream in the extraction channel with respect to the volume of the sample stream, which means include a product stream outlet smaller than required to allow the entire extraction stream to exit coupled with a by-product stream outlet large enough to handle the excess extraction stream. Extraction devices of this invention may comprise multiple product stream outlets so that product streams comprising different types of desired particles may be recovered.

The devices of this invention may be utilized as a sample pretreatment system for an analytical system including sensing means for detecting desired particles in the product stream. Such means include means for mixing the product stream with an indicator stream which interacts with the desired particles so as to allow them to be detected by sensing means known to the art, including optical means, such as optical spectroscopic equipment, and other means such as absorption spectroscopic equipment or means for detecting fluorescence, chemical indicators which change color or other properties when exposed to the desired particles of analyte, immunological means, electrical means, e.g., electrodes inserted into the device, electrochemical means, radioactive means, or virtually any microanalytical technique known to the art including magnetic resonance equipment or other means known to the art to detect the presence of analyte particles such as ions, molecules, polymers, viruses, DNA sequences, antigens, microorganisms, or other factors. Preferably, optical or fluorescent means are used, and antibodies, DNA sequences and the like are attached to fluorescent markers. Indicators and microfabricated mixing means, as well as detection and sensing means are described in U.S. application Ser. No. 08/625,808 incorporated herein by reference.

In one embodiment of this invention the differential extraction device described above is integrated into an analytical system comprising means for further processing the product and/or by-product streams, such as diffusion-based mixing devices for mixing the product stream with an indicator substance (e.g., as described in U.S. application Ser. No. 08/625,808 incorporated herein by reference), and detection chambers wherein the presence of desired analyte particles may be detected. These additional processing means are preferably incorporated with the differential extraction device in a "lab-on-a-chip", fabricated on a standard silicon wafer. The system may comprise quantitation means for determining the concentration of the analyte particles (desired or undesired particles) in the product and/or by-product stream and/or determining the concentration of the analyte particles in the sample stream. Such means include spectroscopic equipment, potentiometric, amperometric, and dielectric relaxation equipment. Concentration determinations can be made by calculation or calibration by means known to the art and disclosed herein.

In another embodiment of this invention used for purification of fluids, e.g., waste-water treatment, hemodialysis, blood detoxification, large volumes, e.g., about 10 ml/sec of sample stream may be treated. In this embodiment, preferably the width of the extraction channel is large, e.g., up to about one meter, although as discussed above, there in no fixed theoretical maximum for the channel width. For treatment of large fluid volumes, devices of this invention, including microfabricated devices, may be connected in parallel, and optionally also in series.

It may be preferable to pre-treat the device, i.e., pre-coat the internal walls of the device to enhance performance, as will be illustrated in the Examples below. The walls can be coated with the sequestering material to be used, before the device is used to effect separation of the desired particles. Without wishing to be bound to any particular theory, it is believed that pre-coating the walls with the sequestering material prevents further adherence of sequestering material to the walls when the sample and sequestering material are later introduced into the device. Alternatively, the internal walls of the device can be pre-coated to effect surface passivation with hydrophilic coating materials, which are commercially available and include, but are not limited to, albumins (e.g., bovine serum albumin, lact albumin and human serum albumin), and art-known silanizing reagents, preferably polyethyleneglycol silanes.

As will be appreciated by those skilled in the art, numerous substitutions may be made for the components and steps disclosed herein, and the invention is not limited to specific embodiments discussed.

BRIEF DESCRIPTION OF THE DRAWINGS

FIG. 7, comprising FIGS. 7A–7D, illustrates diffusion in the extraction device of FIG. 5 as time progresses.

FIG. 8, comprising FIGS. 8A–8D, illustrates diffusion in the extraction device of FIG. 6 as time progresses.

DETAILED DESCRIPTION OF THE PREFERRED EMBODIMENTS

Diffusion of small molecules occurs rapidly over typical microfabricated dimensions. The relationship between the size of a particle, r, the diffusion coefficient, D, and temperature, T, was discovered by Einstein and for the simplest case, spherical particles, this can be written as:

$$D = \frac{k_b T}{6\pi\mu r}.$$

The characteristic distance, l, which a particle with diffusion coefficient D will diffuse in time, t, is $$l = \sqrt{Dt}.$$

Table 2 gives some typical diffusion coefficients and characteristic times.

TABLE 2

Some typical values for different sized particles and molecules. The characteristic time to diffuse 10 µm is given.

| Particle | D (20° C.) | t |
|---|---|---|
| 0.5 µm sphere | $5 \times 10^{-9}$ cm²/sec | 200 sec |
| Protein (hemoglobin) | $7 \times 10^{-7}$ cm²/sec | 1 sec |
| Small Molecule (fluorescein) | $5 \times 10^{-6}$ cm²/sec | 0.2 sec |

Figure 1:
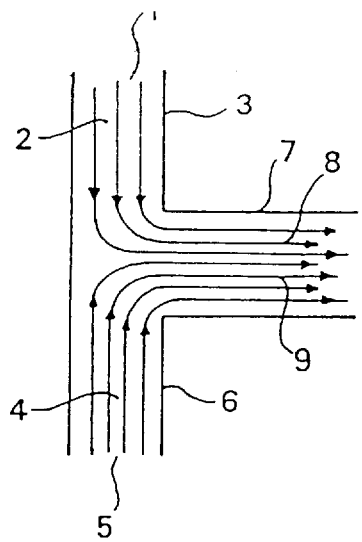
FIG. 1 illustrates a microchannel configuration showing laminar flow of two input streams having a low Reynolds number.

As shown in FIG. 1, in microchannels of small enough dimensions, inertial effects are negligible, such that a sample stream 2 entering a sample stream inlet 1 can flow from a sample stream channel 3 into an extraction channel 7 without mixing with an extraction stream 4 entering an extraction stream inlet 5 and flowing from an extraction stream inlet channel 6 into extraction channel 7. The two streams in the extraction channel 7 form a laminar sample stream 8 and a laminar extraction stream 9.

Figure 2:
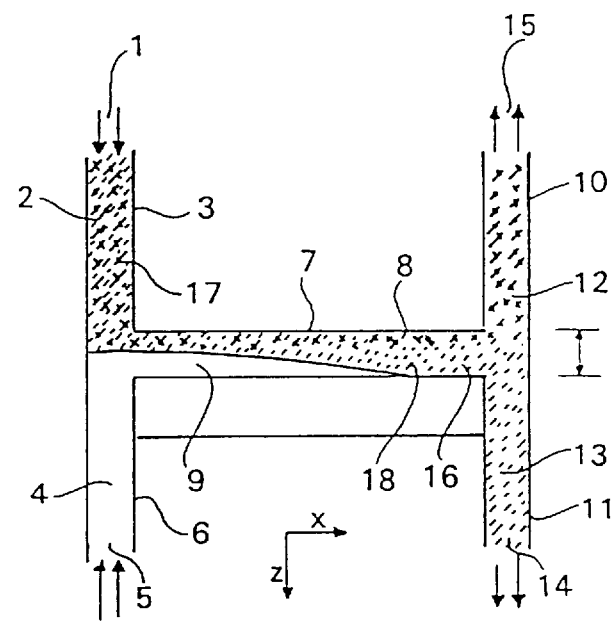
FIG. 2 illustrates a microchannel configuration showing the diffusion of smaller particles from a sample stream into an extraction stream.

In FIG. 2, the arrows at the upper left show the direction of flow in sample stream channel 3 of sample stream 2 entering sample stream inlet 1, and the arrows at the lower left show the direction of flow in extraction stream inlet channel 6 of extraction stream 4 entering extraction stream inlet 5. Sample stream 2 contains larger ("undesired") particles 17 and smaller ("desired") particles 18 (shown by cross-hatching). The sample stream 2 and extraction stream 4 come together in laminar flow in extraction channel 7 to form laminar sample stream 8 and laminar extraction stream 9 and the smaller desired particles 18 begin to diffuse from laminar sample stream 8 into laminar extraction stream 9 to form laminar product stream 16 which contains diffused smaller desired particles 18. The laminar sample stream 8 flows into by-product outlet channel 10 to form by-product stream 12, and leaves the channel through by-product outlet 15. The laminar extraction stream 9 receives smaller desired particles 18 diffused from laminar sample stream 8 and becomes laminar product stream 16 which, in product outlet channel 11, becomes product stream 13 and leaves the channel through product outlet 14.

Figure 3:
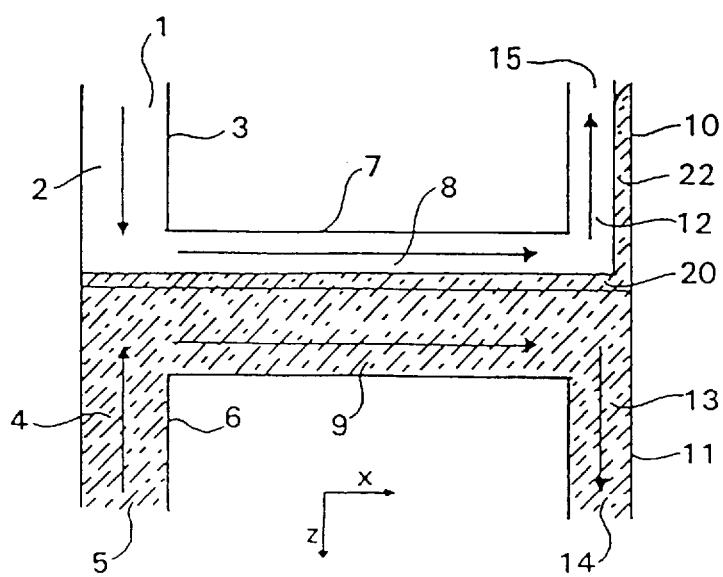
FIG. 3 illustrates a microchannel configuration showing the formation of a fluid barrier between a sample stream and an extraction stream.

In FIG. 3, the direction of the arrow at the upper left shows the direction of flow in sample stream channel 3 of sample stream 2 entering through sample stream inlet 1. The direction of the arrow at the lower left shows the direction of flow in extraction stream inlet channel 6 of extraction stream 4 entering through extraction stream inlet 5. Extraction stream 4 is indicated by cross-hatching. The upper arrow in extraction channel 7 shows the direction of flow of laminar sample stream 8 and the lower arrow in extraction channel 7 shows direction of flow of laminar extraction stream 9. When the volume of extraction stream 4 is greater than the amount which can exit through product outlet channel 11 and product outlet 14, part of laminar extraction stream 9 exits through by-product outlet channel 10 and by-product outlet 15 as excess extraction stream 22. This excess extraction stream 22 is in laminar flow in extraction channel 7 and forms fluid barrier 20. Smaller desired particles 18 (not shown in FIG. 3; see FIG. 2) in the sample stream 2 diffuse from laminar sample stream 8 through fluid barrier 20 into laminar extraction stream 9 to form product stream 16 (not shown in FIG. 3; see FIG. 2).

A simple calculation shows that few particles or molecules with diffusion coefficients smaller than $D = w_{fb}^2 \overline{V}/L$ will be found in the exiting product stream, where $w_{fb}$ is the width of the fluid barrier, $\overline{V}$ is the average flow velocity of the laminar sample stream and L is the length of the extraction channel. Particles or molecules with diffusion coefficients larger than $D = w^2 \overline{V}/L$, where w is the width of the extraction channel, will be in the exiting product stream in the same concentration as in the by-product stream.

Means for injecting feed liquid into the device are provided, as when the device of this invention is used as part of an analytical system. Such means include standard syringes and tubes (fixed volumes per unit time) and tubes (fixed pressure). Means for removing fluid from the product exit may also be provided, including receptacles for the fluid, inducing flow by capillary attraction, pressure, gravity, and other means known to the art as described above. Such receptacles may be part of an analytical or other device for further processing the product stream.

Figure 4:
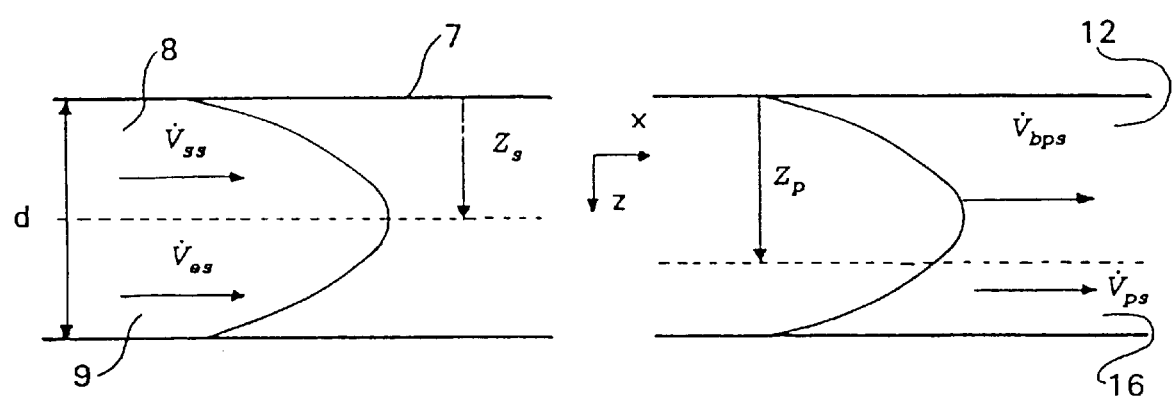
FIG. 4 is a diagram of the inlet and outlet interface streamline in the extraction channel showing the flow rates of the sample, extraction, product and by-product streams.

FIG. 4 shows the extraction channel 7 with laminar extraction stream 9 moving at a velocity $V_{es}$, and laminar sample stream 8 moving at a velocity $V_{ss}$, and having a stream height, (diffusion direction coordinate) $Z_s$ defining the interface streamline location (dotted line) between the laminar sample stream 8 and the laminar extraction stream 9 near the entrance of the extraction channel 7. The combined height of both streams, and thus the depth of the extraction channel 7, is shown as d. The curved line indicates the shape of the velocity profile. As the streams move along the length of the extraction channel 7, laminar sample stream 8 becomes by-product stream 12 moving with a velocity $V_{bps}$ and having a stream height (diffusion direction coordinate) $Z_p$ defining the interface streamline location (dotted line) between the by-product stream 12 and the product stream 13. Laminar extraction stream 9 becomes product stream 13 moving with a velocity $V_{ps}$.

Several steps commonly performed in the chemical assay of a fluid mixture are: (1) precise mixture dilution; (2) extraction of a specific constituent; (3) precise mixing of indicator reagents or test probes (e.g., fluorescently tagged polymer beads); and (4) non-invasive detection of the indicator or probe (e.g., absorbance or fluorescence spectroscopy).

Figure 5:
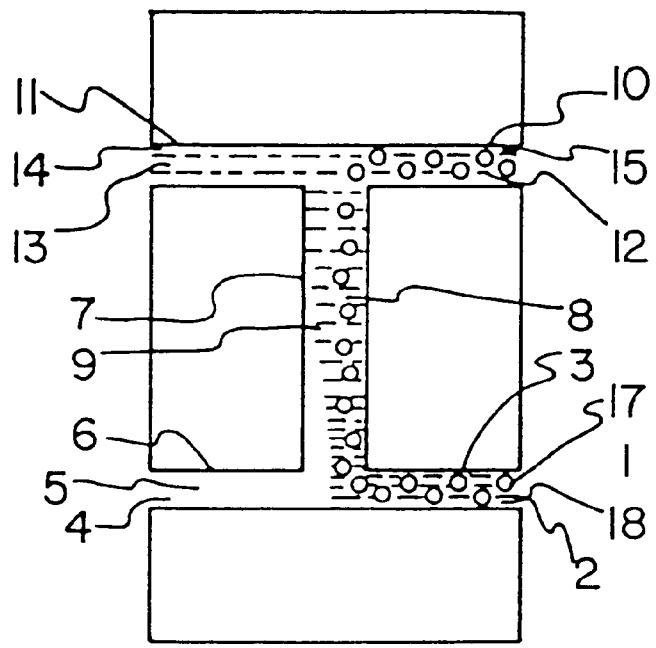
FIG. 5 illustrates an extraction device without sequestering material.

FIG. 5 illustrates an extraction device without sequestering material. A sample stream 2 containing smaller, desired particles 18 and larger, undesired particles is introduced/injected via sample stream inlet 1. An extraction stream 4, e.g., an aqueous buffered solution, is introduced/injected via extraction stream inlet 5. The two streams flow in laminar fashion through extraction channel 7, during which time smaller particles 18 from the sample stream diffuse across the extraction channel into the extraction stream 4, as a result of a concentration gradient. Other gradients can be used, e.g., magnetic, electrical, and centrifugal force. Product stream 13, containing at least some smaller particles 18, exits product outlet 14. By-product stream 12 containing larger particles 17 and smaller particles 18, both from the sample stream, exits by-product outlet 15. If equal flow rates and volumes of the sample stream and extraction stream are used, and if the extraction channel is long enough to allow for complete equilibration to occur, then at most 50% of the small particles in the sample stream will have diffused into the extraction stream and exit the product outlet. With such devices not containing sequestering material, diffusion of small particles into the extraction stream can be increased by injecting a smaller amount of (lower flow rate for) the sample stream than the extraction stream. However, the increase in diffusion is proportional to the ratio of the extraction stream volume/flow rate to that of the sample. Hence the increased efficiency in diffusion as a result of increasing the ratio of the extraction stream volume/flow rate to that of the sample is counteracted by the decreased amount of sample (or flow rate thereof) which can be injected each time.

A concentration profile of the smaller, desired particles 18 diffusing in the device of FIG. 5 is illustrated in FIG. 7 where particle transport occurs by diffusion. The curved line 23 shows concentration versus position of diffusing particles. Time progress from 7A, to 7B, to 7C and equilibration has occurred at illustration 7D. In 7D an equal concentration of small particles is in the two streams (left and right). The concentration in each stream (on both sides, left and right) is 50% of the concentration in the starting sample stream.

With a device not containing sequestering material, the product stream would have to be run through such a device multiple times to achieve a greater than 50% removal of desired particles from the sample stream. For example, a sample would have to be run through such a device 5 times to extract about 97% of the desired small particles, assuming total equilibration were achieved on each run.

The present invention provides increased extraction efficiency by employing a sequestering material in the extraction channel. The sequestering material lowers the effective concentration of the desired particle in the extraction stream, thereby allowing for more rapid and complete diffusion of the desired particles into the extraction stream.

Figure 6:
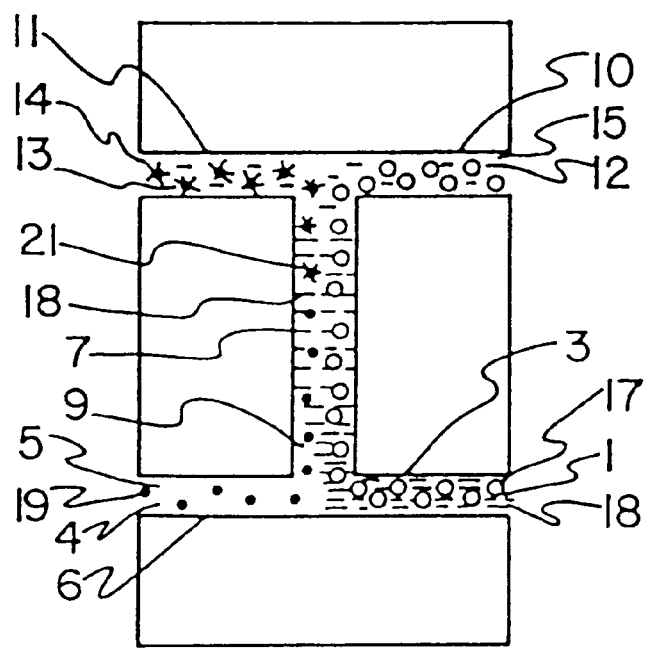
FIG. 6 illustrates an embodiment (the H-filter embodiment) of the extraction device of this invention which includes sequestering material.

FIG. 6 illustrates an embodiment of the present invention. A sample stream containing smaller desired particles 18 shown by dark, shaded areas, and larger undesired particles 17 shown by white circles, is introduced/injected via sample stream inlet 1. An extraction stream 4, containing sequestering material 19, is introduced/injected via extraction stream inlet 5. The two streams flow in laminar fashion through extraction channel 7, during which time smaller desired particles 18 (shown by shaded areas) from the sample stream diffuse across the extraction channel into the extraction stream 4, as a result of a concentration gradient, and bind to the sequestering material, forming a complex 21 of sequestering material bound to desired particles. Additionally, other gradients can be used, e.g., magnetic, electrical, and centrifugal force. Product stream 13, containing at least some smaller desired particles 18, some of which are bound to the sequestering material thereby forming complexes 21, exits product outlet 14. By-product stream 12 containing larger particles 17 and possibly some smaller particles 18, both from the sample stream, exits by-product outlet 15.

The binding constant and amount of the sequestering material in the extraction stream determine the concentration of free desired particles in the extraction stream. Diffusion of desired particles from the sample stream is proportional to the concentration gradient. A sequestering material with a high binding constant for the desired particle provides an effective concentration (or activity) essentially equal to zero, if the binding sites of the sequestering material are in excess compared to the desired particle. Thus, the desired particles continue to diffuse into the extraction stream until the sequestering material is saturated. Only after saturation of the sequestering material does the free concentration of the desired particle begin to equilibrate in the two streams. If an excess of binding sites of the sequestering material is used (compared to the amount of desired particles in the sample), then essentially all of the desired particles are extracted from the sample into the extraction stream.

Both the amount of and the binding constant of the sequestering material for the desired particles affect the efficiency of extraction. The higher the binding constant, the more efficient the extraction will be. In some cases, it may be preferable for the binding to be reversible, e.g., in cases in which it is desirable after extraction of the desired particle to analyze it absent the sequestering material. Preferably the binding constant of the sequestering material is at least $10^{-1}$M or $10^{-2}$M, which is in the range of binding constants for sequestering material with non-specific binding, e.g., activated charcoal. For sequestering material which is specific to a particular type of particle, binding constants of about $10^{-6}$M to about $10^{-8}$M can be preferable; many antibodies bind antigens with binding constants in this range. Essentially irreversible binding occurs at binding constants in the range of $10^{-14}$M to $10^{-15}$M, the latter being the binding constant of biotin to avidin. Those of ordinary skill in the art recognize that even "irreversible" binding can be reversed, e.g., by varying the temperature, pH, and solvent type of the reaction system. Such a reversal of binding (dissociation) is preferable after extraction of the desired particle in cases in which one wants to analyze the desired particles absent the sequestering material.

A concentration profile of the smaller desired particles 18 diffusing in the device of the FIG. 6 is illustrated in FIG. 8. The curved line 23 shows concentration versus position of diffusing particles. Time progress from 8A, to 8B, to 8C, to 8D. In FIG. 8A the desired particles 18 are in the sample stream on the right side of the device, and the sequestering material 19 is in the extraction stream on the left side of the device. FIG. 8B shows that some of the desired particles 18 have diffused across the channel and bound to the sequestering material 19, forming a complex 21. FIG. 8C shows that more of the desired particles 18 have diffused across the channel and bound to the sequestering material 19, forming more of the complex 21. FIG. 8D shows that more of the desired particles 18 have diffused across the channel and bound to the sequestering material 19, forming more of complex 21. The free concentration of desired particles 18 in the extraction stream (left side) is kept extremely low, effectively zero in this case where tight binding occurs between the sequestering material and the desired particles 18. With an excess of sequestering material and a high binding constant, essentially all of the desired particles 18 can be extracted from the sample into the extraction stream.

Figure 9:
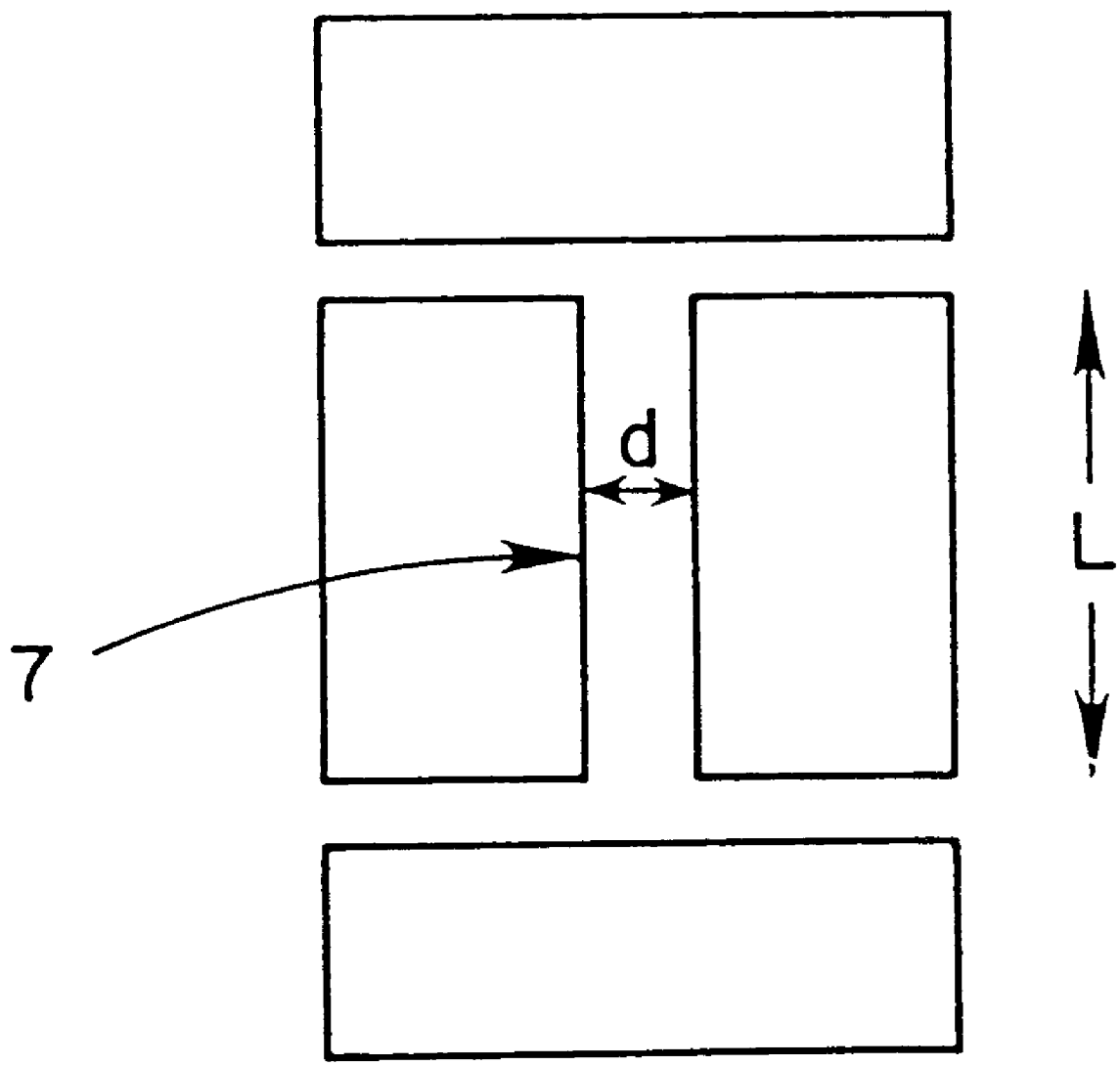
FIG. 9 shows the flow direction (L) and the diffusion/transport direction (depth) of the device of this invention.

The dimensions of the device are chosen so that laminar flow is maintained in the extraction channel. As noted above, and referring to FIG. 9, the flow direction of a channel is called its length (L). The length can be between about 1 centimeter (cm) and about 5 centimeters. The channel dimension in the direction of particle transport (diffusion across extraction channel) at right angles to the length (L) is called its depth (d). The depth is preferably less than about 100 micrometers, and more preferably about 20 micrometers to about 50 micrometers. The third channel dimension at right angles to both the length and depth is called its width (w). In FIG. 9 the width dimension is not shown because it is orthogonal to the plane of the paper. The width can be up to about one meter or greater, including widths of 500 micrometers, 1 mm, 5 cm, and one half meter. The width is large enough to allow passage of the any particles in the streams, including sequestering material. A large width allows for large volumes to be processed in the device. The width can be quite large, e.g., one meter or larger, as long as the diffusion direction (depth) is small enough to maintain laminar flow, and the length is long enough to allow effective diffusion to occur.

Figure 10:
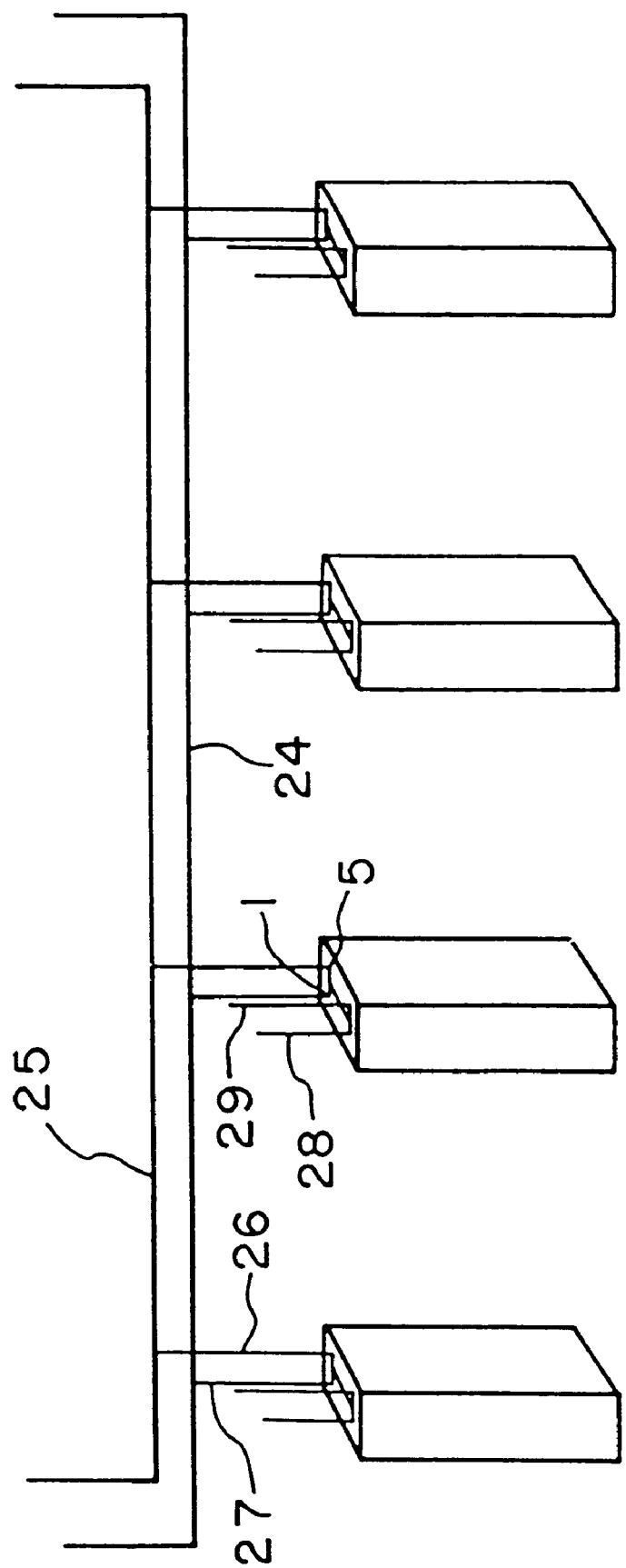
FIG. 10 shows one embodiment of this invention in which a plurality of the extraction devices are connected in parallel.

Large sample volumes can be processed by the device of this invention by one of at least two configurations. The first, mentioned above, is to use a large width in the device, so that the device holds a large volume of fluid. Second, a plurality of, i.e., two or more, devices can be joined in parallel so that a portion of the sample is processed in each device at the same time. FIG. 10 illustrates a configuration with several extraction devices in parallel, the sample stream inlet 1 of each device in fluid connection via sample connector 27 with a sample manifold line 24, and the extraction stream inlet 5 of each device in fluid connection via extraction connector 26 with an extraction manifold line 25. By-product stream exits via by-product outlet line 28, and product stream exits via product outlet line 29. All of the by-product outlet lines 28 can be connected and flow into one reservoir. All of the product outlet lines 29 can be connected and flow into another, single reservoir. In FIG. 10 the devices are illustrated with a width much larger than the depth and length. This relatively large width is optional and can be employed in addition to, or instead of, connecting several devices in parallel, to increase the sample volume processed per unit of time.

Figure 11:
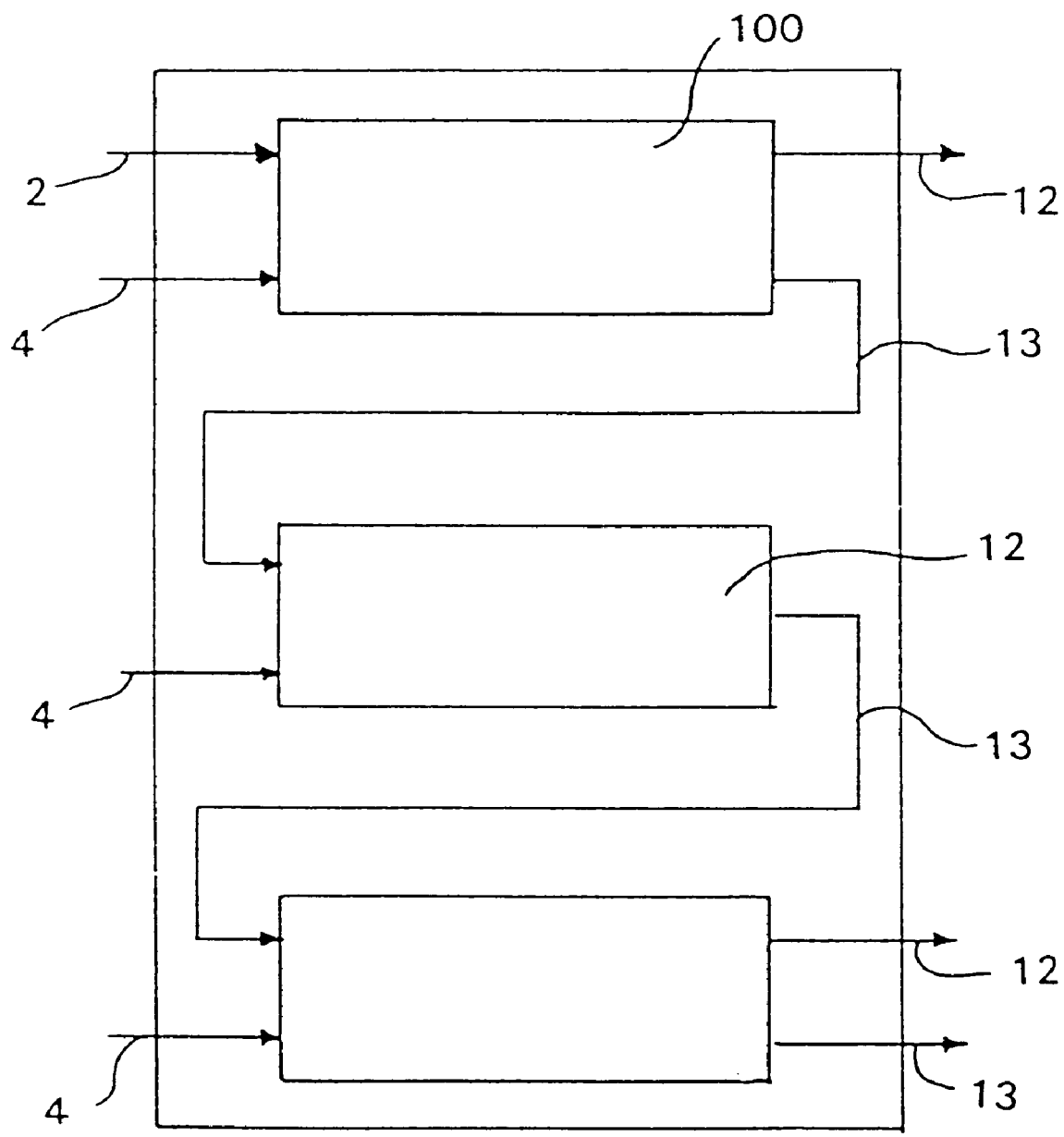
FIG. 11 shows one embodiment of this invention in which a plurality of the extraction devices are connected in series.

A plurality of devices can be connected in series to improve particle separation, i.e., the product stream exiting being in fluid connection with the sample stream inlet of another device, as shown in FIG. 11. In FIG. 11, each extraction device is labeled 100. The by-product stream 12 exits each device and the product stream 13 becomes the sample stream for the next device in series.

Figure 12:
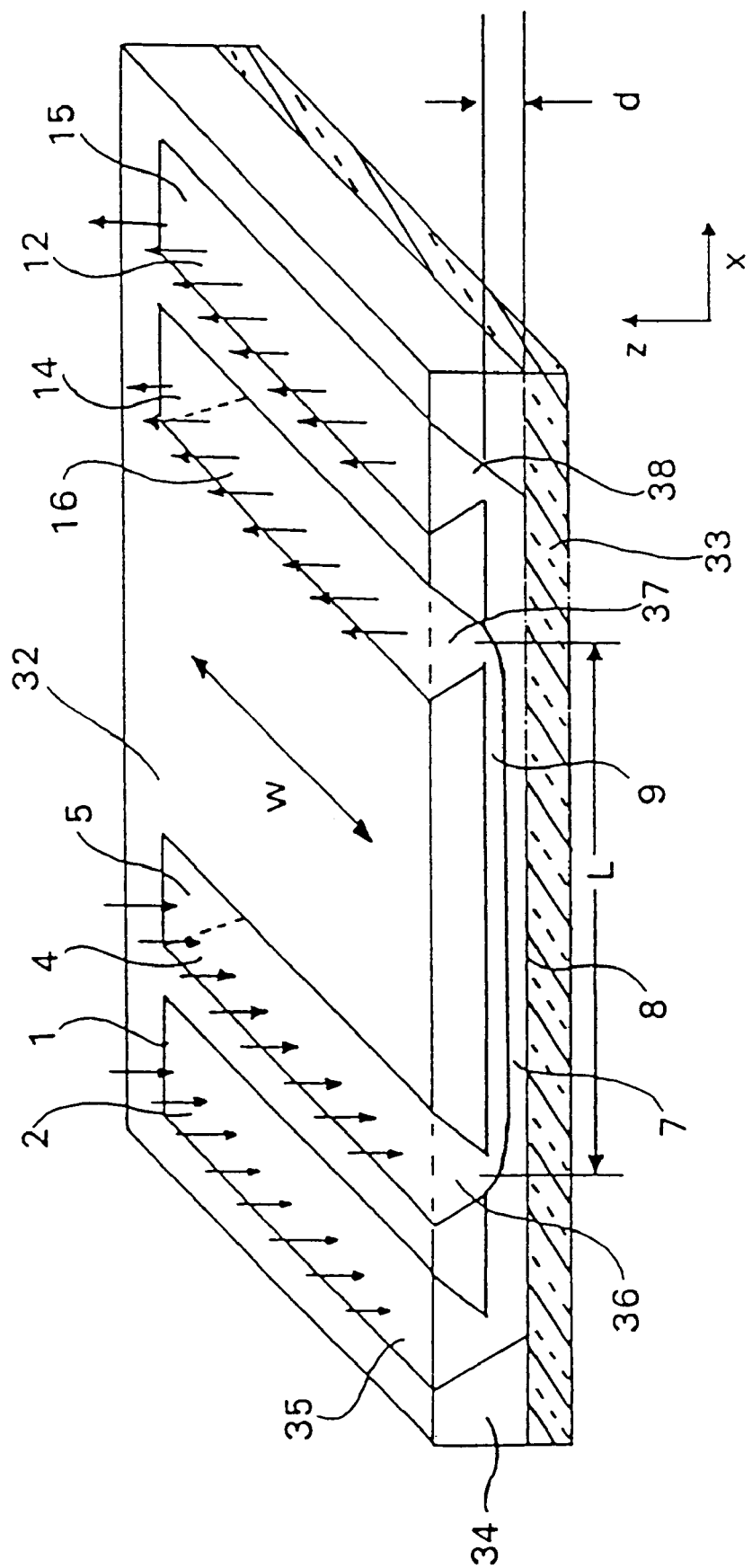
FIG. 12 shows a perspective view of microfabricated flat diffusion extraction device with the diffusion direction rotated 90° from the "H" design shown in FIGS. 1–3, 5 and 6.
Figure 13:
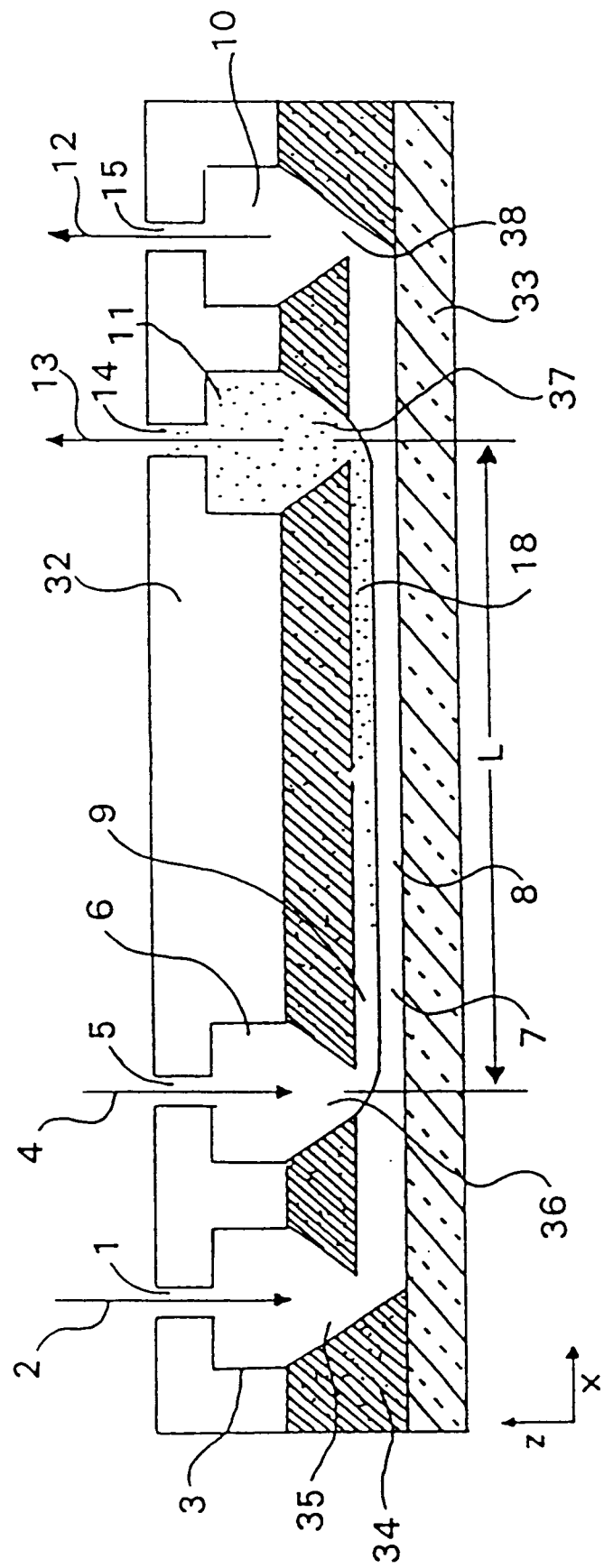
FIG. 13 shows a plan view of the microfabricated flat diffusion extraction system design of FIG. 12.

FIG. 12 shows a perspective view and FIG. 13 shows a plan view of a further embodiment of the invention, a "flat extraction device," in which the diffusion direction in extraction channel 7 is rotated 90° from the embodiments shown in FIGS. 1–3, 5 and 6. This embodiment provides the advantage that the volume of material which can be processed is no longer limited by the width of the extraction channel 7.

The flat extraction device of FIGS. 12 and 13 is made by etching a silicon substrate 34 to provide sample stream inlet groove 35, extraction stream inlet groove 36, product stream exit groove 37, and by-product stream exit groove 38, as well as extraction channel 7. A glass cover 33 serves to enclose extraction channel 7. In FIG. 12, the arrows shown pointing downward into sample stream inlet 1 indicate the flow of sample stream 1. Similarly, the arrows pointing down into extraction stream inlet 5 indicate the flow of extraction stream 4. The arrows pointing up from product outlet 14 indicate the flow of product stream 16, and the arrows pointing up from by-product outlet 15 indicate the flow of by-product stream 12. The length of extraction channel 7 is shown as L and the width of the channels is indicated by the dark arrow as w. The depth of the extraction channel 7 is shown as d. A coupling manifold 32 shown in FIG. 13 with openings extends the depth of sample stream inlet groove 35 to form sample stream channel 3 and sample stream inlet 1, extends the depth of extraction stream inlet groove 36 to form extraction stream channel 6 and extraction stream inlet 5, extends the depth of product stream exit groove 37 to form product outlet channel 11 and product outlet 14, and extending the depth of by-product stream exit groove 38 to form by-product outlet channel 10 and by-product exit 15.

In the flat extraction device shown in FIG. 13 operating by diffusion (concentration gradient) a sample stream 2 shown by the arrow in the upper left enters sample stream inlet 1 and flows in sample stream channel 3. Extraction stream 4 is indicated by an arrow entering extraction stream inlet 5, and flows in extraction stream inlet channel 6. Sample stream 2 flows as a laminar sample stream 8 in extraction channel 7 beneath laminar extraction stream 9. Laminar sample stream 8 is in contact with laminar extraction stream 9 in extraction channel 7 for a length L. Smaller ("desired") particles 18 from laminar sample stream 8 indicated by the stippling in laminar extraction stream 9 flow into product outlet channel 11 as product stream 13 which exits at product outlet 14 as shown by the upward-pointing arrow. By-product stream 12 is the continuation of laminar sample stream 8 past product stream 13. By-product stream 12 contains both the larger ("undesired") particles and a portion of the smaller ("desired") particles which have not diffused into product stream 13. By-product stream 12 flows through by-product outlet channel 10 out through by-product outlet 15.

As noted above, the devices of this invention can be used for hemodialysis. The following discussion points out considerations to be made when designing the devices of this invention and provides an example of removing urea from blood and various details of such a procedure.

When the extraction device of this invention (either H-filter or flat filter embodiment) is used as a blood dialyzer, blood is supplied to the device via a shunt. The flow rate within the device, $F_F$ is determined by the diffusion rate (preferably enhanced by the use of a sequestering material) of the desired particles of interest, as well as the geometry of the device itself. The extraction efficiency of the device depends, in part, on the time that the particles have to diffuse, which determines the maximum overall device flow rate.

The diffusion coefficient of urea is $11.8 \times 10^{-6}$ cm$^2$/s. First, consider the situation where diffusion is not absorption enhanced, i.e., no sequestering material is employed. The following variables used in this example, along with relevant assumptions are:

- $M_U$: Total mass of urea in the body. Generation and excretion will not be considered mathematically in this application, but their affects will be discussed. It is assumed that this value is known (it is easily measurably in dialysis patients).
- $V_B$: Total blood volume (including the volume in the shunt at any moment). This value is typically 5–6 L for adults and 2–3 L for children.
- E: Extraction efficiency of the device. Without sequestering material, this is 0.5 since the final output streams are in equilibrium. The device is designed to allow equilibration (i.e., low enough flow rate so that contact time is high enough for the given geometry).

We are interested in, then, how $M_U$ varies in time. The value of $M_u$ is harder to determine because although we know that any pass through the device removes half of the incident urea, the overall amount in the body is constantly decreasing. From this statement, or from the fact that we must fundamentally be solving Fick's Second Law of Diffusion, we expect the solution to be an exponential decay. One final, crucial assumption is that the blood which returns to the body becomes well-mixed with the rest of the blood. Due to the forceful action of the heart, this is a valid assumption.

The general equation for $M_U$ is:

$$M_U = M_{U(o)} e^{-kt}$$

Taking the derivative with respect to time yields:

$$\frac{dM_U}{dt} = -k M_{u(o)} e^{-kt}$$

Consider this derivative at time=0:

$$\left. \frac{dM_U}{dt} \right|_{t=0} = -k M_{U(o)}$$

As is typical with this type of problem, k is the ratio between the initial mass and the initial rate of action. Since the initial mass is known, k can be determined by finding an expression for the initial rate. The flow rate in the device, $F_F$, represents the rate at which volume from the body is treated in the device. Multiplying by the initial concentration of urea gives the initial treatment rate (initial rate of extraction of desired particles) in the correct units (mass/time). Remembering the extraction efficiency and that this rate must have a negative sign since it represents removal, the initial rate can be written as:

$$\left. \frac{dM_{U(o)}}{dt} \right|_{t=0} = -\left(\frac{M_{U(o)}}{V_B}\right) F_F E$$

where the term in parentheses is the initial concentration. Substituting back into the initial condition equation allows solution for k:

$$k = \left(\frac{F_F}{V_B}\right) E$$

And substituting back into the mass equation yields:

$$M_U = M_{U(o)} e^{-\left[\left(\frac{F_F}{V_B}\right)\right]t}$$

An increase in the coefficient of t means a faster decay, which implies faster removal from the system. Increasing the flow rate in the device, $F_F$, quickens removal of urea since the blood can be treated faster. Increasing the extraction efficiency also quickens removal of urea because the same volume passing through the device is more thoroughly cleansed, i.e., more urea is extracted. Both of these predictions are consistent with the equation. Increasing the total blood volume slows removal since the urea would be more dilute and more volume would have to be treated to achieve the same removal. This prediction is also consistent with the equation.

Considering the example above wherein no sequestering material is employed, the equilibrium condition specifically for urea imposes some limitations on design. Preferably, the diffusion dimension of the device, d, is as small as possible. This serves to reduce diffusion times and increase the upper limit of flow rate. This dimension, however, may be limited by the possible clogging of the channel by red cells (which have a diameter of approximately 8 $\mu$m), and generally is at least about 100 $\mu$m in cases in which the sample is whole blood. The average distance a diffusing molecule must travel for equilibrium is, then, half of this value, or 50 $\mu$m. Consider the equation of Brownian motion:

$$\frac{(\Delta x)^2}{\Delta t} = 2D$$

where D is the diffusion coefficient, which is $11.8 \times 10^{-6}$ cm$^2$/s for urea. Solving for average diffusion time yields a value of $\Delta t = 1.06$ s. This is the lower limit of contact time for the two streams. For the purposes of the following calculation, we chose a length of the device, L, to be 10 mm. In this case, the fluid must travel 10 mm in no less than 1.06 seconds, yielding a maximum average velocity:

$$\overline{V} = \frac{L}{\Delta t} = \frac{10 \text{ mm}}{1.06 \text{ s}} = 9.434 \frac{\text{mm}}{\text{s}}$$

Flow rate is the product of average velocity and cross-sectional area. Because the amount of time the blood needs to be in contact with the extraction stream is to be determined, only the half of the channel which is introducing blood is considered.

A fundamental difference between the H-filter embodiment and the flat filter embodiment is the width dimension, w. In the H-filter, the width is preferably about 50 $\mu$m if the substrate is silicon. In the flat filter, as discussed above, the width is theoretically limitless, and a width of about 1 meter is contemplated.

The contact time necessary for hemodialysis without sequestering material, as well as the number of devices needed in parallel in order to decrease the necessary contact time, in both the H-filter embodiment and flat filter embodiment are compared below. Then the effects of various extraction efficiencies are provided for comparison.

In an H-filter embodiment wherein w=50 $\mu$m, the flow rate is:

$$F_F = \overline{V} \cdot w \cdot \frac{d}{2} =$$

$$\left(9.434 \ \frac{mm}{s}\right)\left(\frac{1 \times 10^3 \ \mu m}{mm}\right)(50 \ \mu m)\left(\frac{100 \ \mu m}{2}\right) = 2.358 \times 10^7 \ \frac{\mu m^3}{s}$$

Converting to standard units yields a flow rate of $2.358 \times 10^{-5}$ ml/s. This value can be substituted into the mass-removal equation above. A slight rearrangement of that equation is useful:

$$\frac{M_U}{M_{U(o)}} = e^{-\left[\left(\frac{F_F}{V_B}\right)E\right]t}$$

The left-hand-side now represents the fraction remaining (FR, current mass divided by initial mass). A target fraction can be chosen and the necessary contact time calculated. Generally, the target for such an exponential process is 99% completion, which corresponds to 0.01 FR. Using the above value of $F_F$, and E=0.5 and $V_B$=5L for a typical adult, the time is $1.953 \times 10^9$ seconds, or 61.9 years. Alternatively, a target time of 4 hours (an estimate based upon typical hemodialysis session length) can be chosen and the necessary $F_F$ can be calculated. Multiple H-filters can be connected in parallel. Dividing by our single-device flow rate determines the number of H-filters required. A contact time of 4-hours requires an $F_F$ of 3.198 ml/s. Dividing by our single-device rate of $2.358 \times 10^{-5}$ ml/s predicts the requirement of over 130,000 H-filters in parallel. This illustrates the advantage of using a sequestering material in an H-filter extraction device to increase extraction efficiency.

Figure 14:
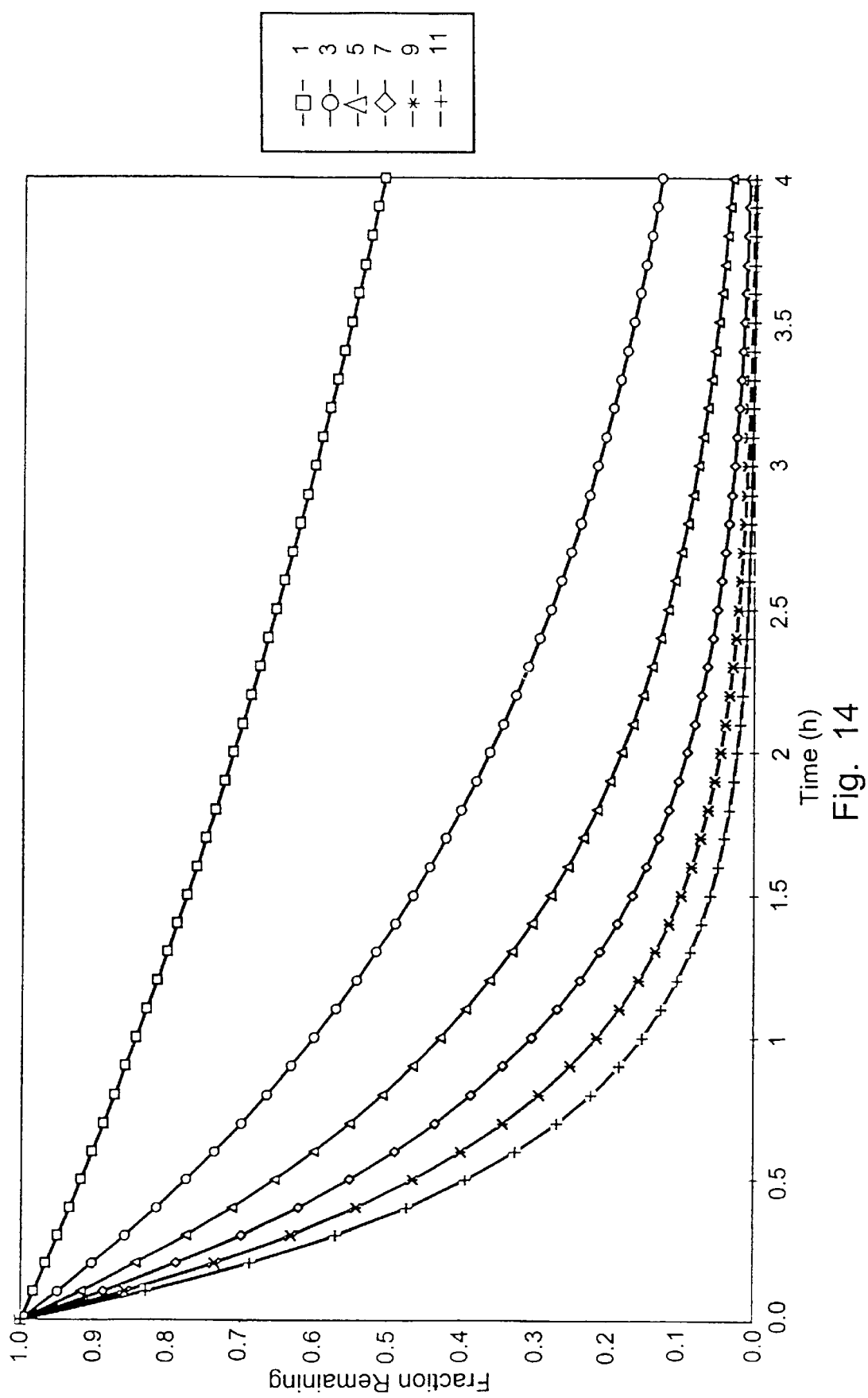
FIG. 14 is a graph showing the fraction of urea remaining after treatment versus time as a function of various numbers of flat filters connected in parallel.

For comparison, consider a flat filter width of 1 meter, which effectively scales the H-filter by a factor of 20,000 (without the use of sequestering material). This increases the single-device flow rate, $F_F$, to 0.4716 ml/s, or 28.30 ml/min, or 1.7 L/hr. The 5 liters is not considered a "serial" volume, so the 1.7 liters cannot simply be divided into 5 to determine treatment time. We must revert to the mass equation, and the target FR of 0.0 1. Using the flat filter flow rate, E =0.5 and a blood volume of 5 liters, the necessary contact time (treatment time) is 97,650 seconds or 27.1 hours. The use of several flat filters in parallel can decrease the necessary contact time. A target time of 4 hours yields a necessary flow rate of 3.198 ml/s (the same as in the H-filter case). This predicts the need for 7 flat filters in parallel. Alternatively, a single flat filter with a width of 7 meters is considered. However, this seems less preferable from a design standpoint. The effect of multiple flat filters is parallel (with no sequestering material) is illustrated in FIG. 14. The fraction of urea remaining decreases as the number of flat filters in parallel increases.

Figure 15:
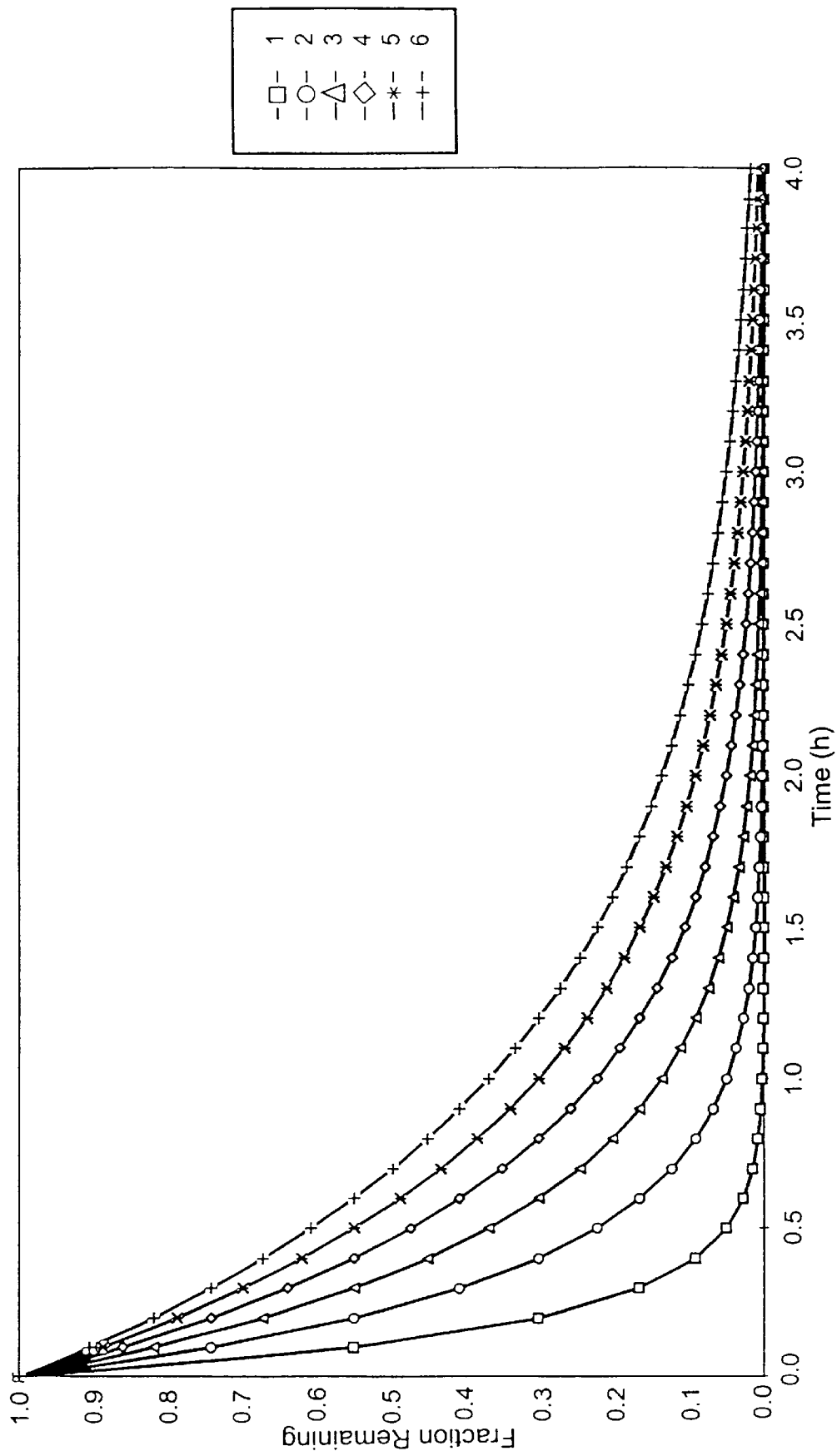
FIG. 15 is a graph showing the fraction of urea remaining after treatment versus time as a function of total blood volume in liters.

Total blood volume, $V_B$, is an important factor in the mass removal equation. Patient blood volume can range realistically from 1 liter to 6 liters, ranging from infants to children to adults. The effect of total blood volume when using 7 flat filters in parallel (with no sequestering material) is illustrated in FIG. 15. The fraction of urea remaining decreases as the total blood volume decreases.

Figure 16:
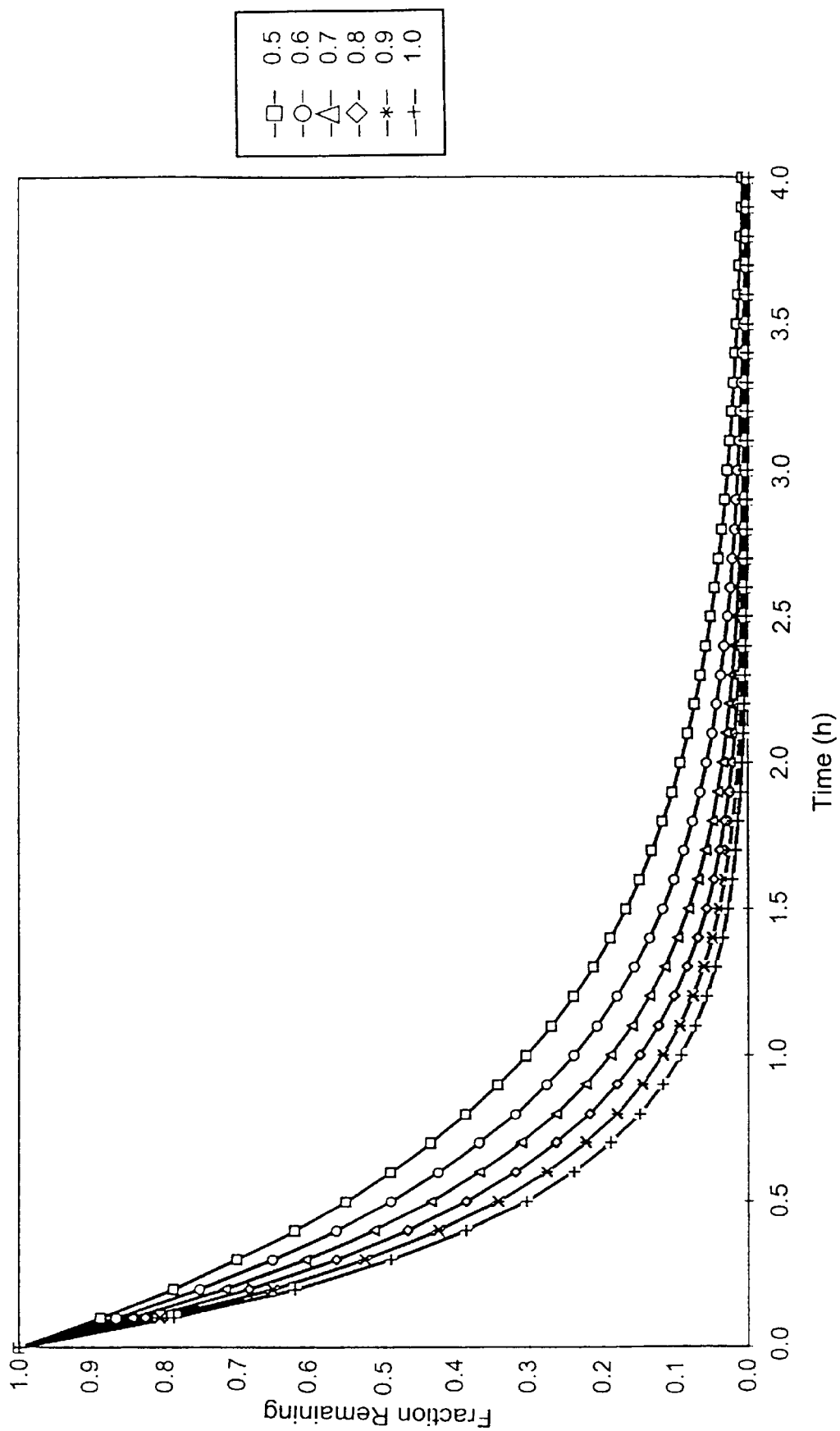
FIG. 16 is a graph showing the fraction of urea remaining after treatment versus time as a function of extraction efficiency.

FIG. 16 illustrates the effect of increasing extraction efficiency when using 7 flat filters in parallel. The fraction of urea remaining decreases as the extraction efficiency of the sequestering material increases.

In the flat filter embodiment, it may be preferable to choose an extraction channel length greater than 10 mm. A preferred embodiment is one in which the length is 50 cm and the width is 50 cm. This makes the filter a square shape comparable in size to current hemodialysis machines. Moreover, it increases the maximum possible flow rate by a factor of 25, which decreases the 0.01 fraction time from 27.1 hours to 1.1 hours. The possibility of shearing of cells at high flow rates must be considered.

When considering extraction efficiencies less than 1.0, a commonly suggested notion is to place multiple flat filters in series, rather than parallel. Consider a case wherein E=0.5. Two flat filters in parallel increases E to 0.75 because only one quarter of the original urea would remain. When considering the decrease in the time constant, this is an improvement factor of 1.5. However, if the same two devices are connected in parallel (each with E=0.5), the improvement factor is 2.0 since the flow rate is doubling. Thus, it is preferable to connect multiple devices in parallel rather than in series in order to increase extraction efficiency.

Numerous embodiments besides those mentioned herein will be readily apparent to those skilled in the art and fall within the range and scope of this invention. All references cited in this specification are incorporated in their entirety by reference herein. The following examples illustrate the invention, but are in no way intended to limit the invention.

EXAMPLES

Example 1

An extraction device was prepared by etching a silicon wafer using techniques known in the art (Brody and Yager, *Solid State Sensor and Actuator Workshop* Hilton Head, S.C. Jun. 2–6, 1996). The channel length was approximately 100 $\mu$m, the channel depth (diffusion dimension) was approximately 15 $\mu$m, and the channel width was approximately 10 $\mu$m. FITC (fluorescein) labeled biotin (Sigma Chemical #B8889) (0.5 $\mu$g/ml) in distilled water was conducted into the sample stream inlet. Rhodamine labeled avidin (Sigma Chemical #A3026) (160 $\mu$g/ml) in distilled water was conducted into the extraction stream inlet. The flow rate through the extraction channel was approximately 100 picoliters/sec. It is known to those in the art that approximately 1 mg of avidin binds 10–15 $\mu$g of biotin. The rhodamine labeled avidin was observed moving at a rate substantially less than the flow rate, and it was determined that it was adhering to the walls of the channel, inlets and outlets.

To counteract this adhering of the avidin to the walls, the amount of avidin needed to coat the walls of the device uniformly with a monolayer of avidin was calculated. The device had a volume/surface area ratio of about 10 $\mu$m. A 1 mg/ml solution of avidin was calculated to be the minimum amount needed to cover the walls of a device with a volume/surface area ratio of about 10 $\mu$m, assuming that all of the avidin would be adsorbed by the walls. (The internal volume of the device was calculated to be 15 picoliters, and thus this is the volume of solution needed to fill the device and coat the walls.) A solution of avidin (0.17 mg/ml) (which was ⅙ the concentration of a 1 mg/ml solution) in distilled water was introduced into the device in 6 aliquots. The avidin coated front was moving at a rate approximately ⅙ the average flow rate, thereby indicating that avidin was adhering to the walls.

Example 2

The device with its walls substantially completely and uniformly coated with avidin (prepared in Example 1) was used in Example 2. A solution (10 $\mu$L) of streptavidin immobilized on 1 $\mu$m iron oxide particles (Sigma Chemical #S2415) in distilled water was introduced into the extraction stream inlet. A solution of biotin (Sigma Chemical #B8889) (10 ng/ml) in distilled water was conducted into the sample stream inlet. It was apparent to the naked eye that biotin became concentrated in the extraction stream. However, the fluorescence was low because the number of molecules of streptavidin immobilized on the iron oxide was small, necessitating a low biotin concentration in order to maintain a stoichiometric excess of streptavidin. Additionally, streptavidin partially quenches the fluorescent marker (FITC), making fluorescent measurements more difficult.

To improve fluorescent measurements, the device is preloaded with a polyethyleneglycol silane to achieve surface passivation. A streptavidin with a longer arm prior to its binding site for biotin helps prevent quenching of fluoroscein.

What is claimed is:

1. A device for enhancing differential transport of desired particles from a sample stream containing said desired particles into an extraction stream, said device comprising:
   a. a sample stream inlet;
   b. an extraction stream inlet;
   c. a flow channel in fluid communication with said sample stream inlet and said extraction stream inlet for receiving a sample stream from said sample stream inlet in adjacent laminar flow with an extraction stream from said extraction stream inlet;
   d. a sequestering material within said flow channel for capturing desired particles in said extraction stream; and
   e. at least one outlet in fluid communication with said flow channel.

2. The device of claim 1 made by a microfabrication process.

3. A device of claim 1 wherein said sequestering material is an adsorbent material.

4. A device of claim 1 wherein said sequestering material is an absorbent material.

5. A device of claim 1 wherein said sequestering material is effectively non-diffusing in said device.

6. A device of claim 1 comprising desired particles reversibly bound to said sequestering material.

7. A device of claim 1 wherein said product contains greater than 50% of said desired particles in said sample stream.

8. A device of claim 1 wherein said product contains greater than 75% of said desired particles in said sample stream.

9. A device of claim 1 wherein substantially all of said desired particles are removed from said sample stream.

10. A device of claim 1 having a width of between about 2 micrometers and one meter.

11. A device of claim 1 having a width between about 5 micrometers and 5 centimeters.

12. A device of claim 1 having a width between about 10 micrometers and 100 micrometers.

13. An analytic system comprising a device of claim 1 in combination with means for detecting the presence of said desired particles captured by said sequestering material.

14. An analytic system comprising a device of claim 1 in combination with means for detecting the presence of an analyte in a by-product stream from which desired particles have been removed.

15. A system comprising a device of claim 1 in combination with means for removing said sequestering material with said captured desired particles from said product stream.

16. An analytic system comprising a device of claim 13 in combination with means for detecting the presence of an analyte in a product stream from which desired particles and sequestering material have been removed.

17. An apparatus containing a plurality of devices of claim 1.

18. A method for enhancing differential transport of at least a portion of desired particles from a sample stream comprising said desired particles into an extraction stream, said method comprising the steps of:
   a) introducing said sample stream into the sample stream inlet of an extraction device comprising:
      i) a sample stream inlet;
      ii) an extraction stream inlet;
      iii) a flow channel in fluid communication with said sample stream inlet and said extraction stream inlet for receiving a sample stream from said sample stream inlet in adjacent laminar flow with an extraction stream from said extraction stream inlet;
      iv) a sequestering material within said flow channel for capturing desired particles in said extraction stream; and
      v) at least one outlet in fluid communication with said flow channel;
   b) introducing an extraction stream into the flowchannel of said extraction device; and
   c) introducing into said extraction channel a sequestering material for capturing the desired particles such that the desired particles are captured by the sequestering material.

19. The method of claim 18 wherein said sample stream is blood and said desired particles are toxin particles.

20. The method of claim 18 wherein said desired particles are particles of a substance which interferes with analysis of said sample stream.

21. The method of claim 18 wherein said sequestering material comprises polymeric beads.

22. The method of claim 18 wherein said sequestering material comprises an enzyme which binds to said desired particles.

23. The method of claim 18 wherein said sequestering material is an absorbent material.

24. The method of claim 18 wherein said sequestering material is a substantially non-diffusing high molecular weight polymer.

25. The method of claim 18 wherein before performing steps a, b, and c, the device is pre-coated with a hydrophilic material by injecting the hydrophilic material into the sample stream inlet and extraction stream inlet.

26. The method of claim 18 wherein a major portion of said desired particles are transported from said sample stream into said extraction stream.

* * * * *